(12) United States Patent
Boehnlein et al.

(10) Patent No.: US 6,776,986 B1
(45) Date of Patent: Aug. 17, 2004

(54) INHIBITION OF HIV-1 REPLICATION BY ANTISENSE RNA EXPRESSION

(75) Inventors: Ernst Boehnlein, Randolph, NJ (US); Sonia Escaich, Paris (FR); Heini Ilves, Palo Alto, CA (US); Gabor Veres, Palo Alto, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/194,300
(22) PCT Filed: Jun. 6, 1997
(86) PCT No.: PCT/EP97/02952
   § 371 (c)(1),
   (2), (4) Date: Nov. 23, 1998
(87) PCT Pub. No.: WO97/46673
   PCT Pub. Date: Dec. 11, 1997

Related U.S. Application Data
(60) Provisional application No. 60/019,232, filed on Jun. 6, 1996.

(51) Int. Cl.$^7$ ............................................. A61K 48/00
(52) U.S. Cl. ................. 424/93.21; 536/23.1; 536/24.5; 435/69.1; 435/320.1; 435/325
(58) Field of Search .............................. 536/23.1, 24.5; 424/93.21; 514/44; 435/320.1, 455

(56) References Cited

U.S. PATENT DOCUMENTS

| | | | |
|---|---|---|---|
| 4,999,421 A | * 3/1991 | Brunck et al. | ............... 530/350 |
| 5,276,019 A | 1/1994 | Cohen et al. | |
| 5,324,643 A | 6/1994 | Greatbatch et al. | |
| 5,580,761 A | 12/1996 | Greatbatch et al. | |
| 5,583,035 A | * 12/1996 | Kretschmer et al. | ...... 435/240.2 |
| 5,585,479 A | * 12/1996 | Hoke et al. | ................. 536/24.5 |
| 5,650,306 A | * 7/1997 | Nable et al. | .............. 435/172.3 |
| 5,858,646 A | * 1/1999 | Kang | ............................. 435/5 |
| 5,919,701 A | * 7/1999 | Peterson et al. | ............ 435/375 |
| 6,013,639 A | 1/2000 | Peyman et al. | |
| 6,107,062 A | * 8/2000 | Hu et al. | .................. 435/91.41 |
| 6,121,434 A | 9/2000 | Peyman et al. | |

FOREIGN PATENT DOCUMENTS

| | | |
|---|---|---|
| AU | 711792 | 8/1996 |
| CA | 2077314 | 3/1993 |
| CA | 2135591 | 5/1995 |
| DE | 37 42 049 A1 | 6/1989 |
| EP | 0 263 740 A1 | 4/1988 |
| EP | 0 300 687 A2 | 1/1989 |
| EP | 0 331 939 A2 | 9/1989 |
| EP | 0 386 563 B1 | 9/1990 |
| EP | 0 598 935 A1 | 6/1994 |
| EP | 0 612 844 A2 | 8/1994 |
| EP | 0 653 439 A2 | 5/1995 |
| EP | 0 693 287 A1 | 1/1996 |
| EP | 0 702 084 B1 | 3/1996 |
| FR | 2 687 411 | 8/1993 |
| GB | 2 268 492 A | 1/1994 |

(List continued on next page.)

OTHER PUBLICATIONS

Kohn, The current status of gene therapy using hematopietic stem cells, 1995, Current Science, vol. 7, pp. 56–63.*
Verma et al., Gene therapy–promises, problems and prospects, Sep. 18, 1997, vol. 389, Nature, pp. 239–242.*
Anderson, Human gene therapy, Apr. 30, 1998, Nature, vol. 392, pp. 25–30.*
Branch, A good antisense molecule is hard to find, Feb. 1998, TIBS, pp. 45–50.*
Plenat, Animal models of antisense oligonucleotides: lesson for use in humans, Jun. 1996, Molecular Medicine Today, pp. 250–257.*
Agrawal, In Vivo Pharmacokenetics of Phosphorothioate Oligonucleotides Containing Contiguous Guanosines, 1997, Antisens & Nucleic Acid Drug Development, vol. 7, pp. 245–249.*
Bauer et al. Gene Therapy for pediatric AIDS pp. 318–329 1997.*
Onodera et al. Gene therapy for severe combined immunodeficiency caused by adenosine deaminase deficiency: improved retroviral vectors for clinical trials 1999 pp. 89–96.*
Kohn et al. A clinical trial of retroviral–mediated transfer of a rev–responsive element decoy gene into CD34+ cills from the bone marrow of human immunodeficiency virus–1 infected children vol. 94, No. 1 1999 pp. 368–371.*
Kohn,MD The current status of gene therapy using hematopoietic stem cells pp. 56–63 1995.*
Hoeben et al. Toward gene therapy for hemophilia A: long–term persistence of factor VIII–Secreting fibroblasts after transplantation into immunodeficient mice pp. 179–185 1993.*
Rosenberg et al. Gene therapist, heal thyself pp. 1751 vol. 287 2000.*
Gunzgurg et al. Virus vector design in gene therapy pp. 410–417 vol. 1 No. 9 1995.*
Roman et al. Latest developments in gene transfer technology: achievements, perspectives, and contrversies over therapeutic applications pp. 19–39 2000.*
Hoogerbrugge et al. Bone marrow gene transfer in three patients with adenosine deaminase deficiency pp. 179–183 1996.*
Engel et al. Stem cell directed gene therapy pp. 1093–4715 1999.*
Chatterjee, et al., "Dual–Target Inhibition of HIV–1 in Vitro by Means of an Adeno–Associated Virus Antisense Vector," Science, 258:1485–1488 (Nov. 27, 1992).

(List continued on next page.)

*Primary Examiner*—Dave T. Nguyen
(74) *Attorney, Agent, or Firm*—Susan Hess

(57) ABSTRACT

Novel antisense sequences to the unspliced or single spliced portions of mRNA transcript from HIV-1 provirus, optionally co-expressed with an inhibitory transdominant mutant HIV-1 protein, are found to be useful in the treatment of HIV-1 infection.

30 Claims, 21 Drawing Sheets

FOREIGN PATENT DOCUMENTS

| | | |
|---|---|---|
| JP | 08-154687 | 6/1996 |
| WO | WO 87/03451 | 6/1987 |
| WO | WO 87/07300 | 12/1987 |
| WO | WO 88/09810 | 12/1988 |
| WO | WO 88/10311 | 12/1988 |
| WO | WO 89/08146 | 9/1989 |
| WO | WO 90/12578 | 11/1990 |
| WO | WO 90/13641 | 11/1990 |
| WO | WO 90/14427 | 11/1990 |
| WO | WO 90/15813 | 12/1990 |
| WO | WO 91/04319 | 4/1991 |
| WO | WO 91/04753 | 4/1991 |
| WO | WO 91/11535 | 8/1991 |
| WO | WO 91/17246 | 11/1991 |
| WO | WO 91/18004 | 11/1991 |
| WO | WO 92/06192 | 4/1992 |
| WO | WO 92/20698 | 11/1992 |
| WO | WO 93/09813 | 5/1993 |
| WO | WO 94/01550 | 1/1994 |
| WO | WO 94/02498 | 2/1994 |
| WO | WO 94/02637 | 2/1994 |
| WO | WO 94/08004 | 4/1994 |
| WO | WO 94/10302 | 5/1994 |
| WO | WO 94/16060 | 7/1994 |
| WO | WO 94/16066 | 7/1994 |
| WO | WO 94/17086 | 8/1994 |
| WO | WO 94/17091 | 8/1994 |
| WO | WO 94/17093 | 8/1994 |
| WO | WO 94/21825 | 9/1994 |
| WO | WO 94/26877 | 11/1994 |
| WO | WO 95/00638 | 1/1995 |
| WO | WO 95/01369 | 1/1995 |
| WO | WO 95/03406 | 2/1995 |
| WO | WO 95/03407 | 2/1995 |
| WO | WO 95/04068 | 2/1995 |
| WO | WO 95/05851 | 3/1995 |
| WO | WO 95/18136 | 7/1995 |
| WO | WO 95/18854 | 7/1995 |
| WO | WO 95/27054 | 10/1995 |
| WO | WO 95/27783 | 10/1995 |
| WO | WO 95/30755 | 11/1995 |
| WO | WO 95/31477 | 11/1995 |
| WO | WO 95/32986 | 12/1995 |
| WO | WO 96/02557 A1 | 2/1996 |
| WO | WO 96/04294 | 2/1996 |
| WO | WO 96/04788 | 2/1996 |
| WO | WO 96/23876 | 8/1996 |
| WO | WO 96/23878 | 8/1996 |
| WO | WO 96/27604 | 9/1996 |
| WO | WO 96/29337 | 9/1996 |
| WO | WO 96/32474 | 10/1996 |
| WO | WO 96/35706 | 11/1996 |
| WO | WO 96/36705 | 11/1996 |
| WO | WO 96/37623 | 11/1996 |
| WO | WO 97/46673 | 12/1997 |

OTHER PUBLICATIONS

Cohli, et al., "Inhibition of HIV–1 Multiplication in a Human CD4+ Lymphocytic Cell Line Expressing Antisense and Sense RNA Molecules Containing HIV–1 Packaging Signal and Rev Response Element(s)," Antisense Research and Development, 4:19–26 (1994).

Doglio, et al., esp@cenet—Document Bibliography and Abstract, FR2687411 "Vector Comprising a Viral Gene Transcribed by RNA Polymerasee III, and Process for the Intercellular Production of RNA" (Aug. 20, 1993).

Escaich, et al., "RevM10–Mediated Inhibition of HIV–1 Replication in Chronically Infected T Cells," Human Gene Therapy, 6:625–634 (May 1995).

Federico, et al., "A Replication–Deficient Human Immunodeficiency Virus–1 Genome as an Interference–Inducing Provirus," Antibiot. Chemother., 48:217–225 (1996).

Federico, et al., "Anti–HIV Viral Interference Induced by Retroviral Vectors Expressing a Nonproducer HIV–1 Variant," Acta. Haematol., 95:199–203 (1996).

Gyotoku, et al., "Inhibition of Human Immunodeficiency Virus Replication in a Human T Cell Line by Antisense RNA Expressed in the Cell," Virus Genes, 5(3):189–202 (1991).

Hiroshi, et al., MicroPatent PatSearch, JP08154687, "Anti–Sense Oligonucleotide and Antiviral Agent" (Jun. 18, 1996).

Homann, et al., "Complementary Large Loops Determine the Rate of RNA Duplex Formation in vitro in the Case of an Effective Antisense RNA Directed Against the Human Immunodeficiency Virus Type 1," J. Mol. Biol., 233:7–15 (1993).

Homann, et al., "Extension of Helix II of an HIV–1–Directed Hammerhead Ribozyme with Long Antisense Flanks does not Alter Kinetic Parameters in vitro but Causes Loss of the Inhibitory Potential in Living Cells," Nucleic Acids Research, 22(19):3951–3957 (1.

Homann, et al., "Incorporation of the Catalytic Domain of a Hammerhead Ribozyme into Antisense RNA Enhances its Inhibitory Effect on the Replication of Human Immunodeficiency Virus Type 1," Nucleic Acids Research, 21(12):2809–2814 (1993).

International Search Report, PCT/EP97/02952 (Dec. 2, 1997).

Joshi, et al., "Inhibition of Human Immunodeficiency Virus Type 1 Multiplication by Antisense and Sense RNA Expression," Journal of Virology, 65(10):5524–5530 (Oct. 1991).

Junker, et al., "Reduction in Replication of the Human Immunodeficiency Virus Type 1 in Human T Cell Lines by Polymerase III–Driven Transcription of Chimeric tRNA–Antisense RNA Genes," Antisense Research and Development, 4:165–172 (1994).

Kim, et al., "Inhibition of HIV Replication by Sense and Antisense Rev Response Elements in HIV–Based Retroviral Vectors," Journal of Acquired Immune Deficiency Syndromes and Human Retrovirology, 12:343–351 (1996).

Kretschmer, et al., esp@cenet—Document Bibliography and Abstract, EP0598935, "Expression Vectors and Their Use to Produce HIV–Resistant Human Cells for Therapeutic Use" (Jun. 1, 1994).

Lebleu, et al., esp@cenet—Document Bibliography and Abstract, EP0263740, "Coupling Conjugates Between RNA or DNA Sequences and a Protein, Method for Their Preparation and Their Biological Use" (Apr. 13, 1998).

Meyer, et al., "Inhibition of HIV–1 Replication by a High–Copy–Number Vector Expressing Antisense RNA for Reverse Transcriptase," Gene, 129:263–268 (1993).

Morgan, et al., "Gene Therapy for AIDS Using Retroviral Mediated Gene Transfer to Deliver HIV–1 Antisense TAR and Transdominant Rev Protein Genes to Syngeneic Lymphocytes in HIV–1 Infected Identical Twins," Human Gene Therapy, 7:1281–1306 (Jun. 20, 1996).

Ohkawa, et al., "Multiple Site–Specific Cleavage of HIV RNA by Transcribed Ribozymes from Shotgun–Type Trimming Plasmid," Nucleic Acids Symposium Series No. 29. 121–122 (1993).

Peyman, et al., esp@cenet—Document Bibliography and Abstract, EP0653439, "Stabilized Oligonucleotides and the Use Thereof" (May 17, 1995).

Peyman, et al., esp@cenet—Document Bibliography and Abstract, EP0693287, "RNA Cleaving or Binding Oligonucleotides" (Jan. 24, 1996).

Plavec, et al., "High Trandominant RevM10 Protein Levels are Required to Inhibit HIV–1 Replication in Cell Lines and Primary T Cells: Implication for Gene Therapy of AIDS," Gene Therapy, 4:128–139 (1997).

Renneisen, et al., "Inhibition of Expression of Human Immunodeficiency Virus–1 in Vitro by Antibody–targeted Liposomes Containing Antisense RNA to the env Region," The Journal of Biological Chemistry, 27:16337–16342 (Sep. 25, 1990).

Rhodes, et al., "Inhibition of Human Immunodeficiency Virus Replication in Cell Culture by Endogenously Synthesized Antisense RNA," Journal of General Virology, 71:1965–1974 (1990).

Rittner, et al., "Identification and Analysis of Antisense RNA Target Regions of the Human Immunodeficiency Virus Type a," Nucleic Acids Research, 19(7):1421–1426 (1991).

Rittner, et al., "In Vitro Selection of Fast–hybridizing and Effective Antisense RNAs Directed Against the Human Immunodeficiency Virus Type 1," Nucleic Acids Research, 21(6):1381–1387 (1993).

Sczakiel, et al., "Antisense RNA–Mediated Inhibition of the Replication of the Human Immunodeficiency Virus Type 1," Annals of the New York Academy of Sciences, 660:268–271 (1992).

Sczakiel, et al., "Computer–Aided Search for Effective Antisense RNA Target Sequences of the Human Immunodeficiency Virus Type 1," Antisense Research and Development, 3:45–52 (1993).

Sczakiel, et al., "Inhibition of Human Immunodeficiency Virus Type 1 Replication in Human T Cells Stably Expressing Antisense RNA," Journal of Virology, 65(1):468–472 (Jan. 1991).

Sczakiel, et al., "Replication of the Human Immunodeficiency Virus Type 1 is Inhibited in Human Cells with Antisense RNA Expression," Biochemical Society Transactions, 19:437S (1991).

Sczakiel, et al., "Specific Inhibition of Human Immunodeficiency Virus Type 1 Replication by RNA Transcribed in Sense and Antisense Orientation from the 5–leader/gag Region," Biochemical and Biophysical Research Communications, 169(2):643–651 (Jun. 15, 1.

Sczakiel, et al., "Tat–and Rev–Directed Antisense RNA Expression Inhibits and Abolishes Replication of Human Immunodeficiency Virus Type 1: a Temporal Analysis," Journal of Virology, 66(9):5576–5581 (Sep. 1992).

Tabler, et al., "A Three–Nucleotide Helix I is Sufficient for Full Activity of a Hammerhead Ribozyme: Advantages of an Asymmetric Design," Nucleic Acids Research, 22(19):3958–3965 (1994).

Theurer, K., esp@cenet—Document Bibliography and Abstract, DE 3742049, "Preparation and Use of Vaccines and Diagnostic Aids for Viral Diseases and Cancers" (Jun. 22, 1989).

Tung, et al., "Targeted Inhibition of Immunodeficiency Virus Replication in Lymphocytes Through Retroviral Mediated Gene Transfer," Arch Virol., 133:407–421 (1993).

Vandendriessche, et al., "Inhibition of Clinical Human Immunodeficiency Virus (HIV) Type 1 Isolates in Primary CD4+ T Lymphocytes by Retroviral Vectors Expresinng Anti–HIV Genes," Journal of Virology, 69(7):4045–4052 (Jul. 1995).

Veres, et al., "Comparative Analyses of Intracellularly Expressed Antisense RNAs as Inhibitors of Human Immunodeficiency Virus Type 1 Replication," Journal of Virology, 72(3):1894–1901 (Mar. 1998).

Veres, et al., "Intracellular Expression of RNA Transcripts Complementary to the Human Immunodeficiency Virus Type 1 gag Gene Inhibits Viral Replication in Human CD4+ Lymphocytes," Journal of Virology, 70(12):8792–8800 (Dec. 1996).

Woffendin, et al., "Expression of a Protective Gene Prolongs Survival of T Cells in Human Immunodeficiency Virus–Infected Patients," Proc. Natl. Acad. Sci. USA, 93:2889–2894 (Apr. 1996).

Gabor et al., "Preclinical Study on the Construction, anti–HIV–1 Efficacy and Safety/Toxicity if RevM10–antisense pol (LMSNpolAS) Combination Vector", Novartis Pharma Research, Systemix Inc. , pp. 1–48, (2000).

Gabor Veres et al., "LMSNpolAS Retroviral Vector Combines RevM10 and Antisense Strategies for the Treatment of HIV–1 Infection" Novartis Pharmaceutical Research, Systemix Inc., pp. 1–32, (1998).

* cited by examiner

FIGURE 1

Sequence of HIV-1 HXB2 strain polymerase gene region 1 (2004-3400 bp)

Sense orientation:

GGGCCCCTAGGAAAAAGGGCTGTTGGAAATGTGGAAAGGAAGGACACCAAATGA
AAGATTGTACTGAGAGACAGGCTAATTTTTTAGGGAAGATCTGGCCTTCCTACAAG
GGAAGGCCAGGGAATTTTCTTCAGAGCAGACCAGAGCCAACAGCCCCACCAGAAG
AGAGCTTCAGGTCTGGGGTAGAGACAACAACTCCCCCTCAGAAGCAGGAGCCGAT
AGACAAGGAACTGTATCCTTTAACTTCCCTCAGGTCACTCTTTGGCAACGACCCCT
CGTCACAATAAAGATAGGGGGGCAACTAAAGGAAGCTCTATTAGATACAGGAGCA
GATGATACAGTATTAGAAGAAATGAGTTTGCCAGGAAGATGGAAACCAAAAATGA
TAGGGGGAATTGGAGGTTTTATCAAAGTAAGACAGTATGATCAGATACTCATAGA
AATCTGTGGACATAAAGCTATAGGTACAGTATTAGTAGGACCTACACCTGTCAAC
ATAATTGGAAGAAATCTGTTGACTCAGATTGGTTGCACTTTAAATTTTCCCATTAG
CCCTATTGAGACTGTACCAGTAAAATTAAAGCCAGGAATGGATGGCCCAAAAGTT
AAACAATGGCCATTGACAGAAGAAAAAATAAAAGCATTAGTAGAAATTTGTACAG
AGATGGAAAAGGAAGGGAAAATTTCAAAAATTGGGCCTGAAAATCCATACAATAC
TCCAGTATTTGCCATAAAGAAAAAAGACAGTACTAAATGGAGAAAATTAGTAGAT
TTCAGAGAACTTAATAAGAGAACTCAAGACTTCTGGGAAGTTCAATTAGGAATAC
CACATCCCGCAGGGTTAAAAAAGAAAAAATCAGTAACAGTACTGGATGTGGGTGA
TGCATATTTTTCAGTTCCCTTAGATGAAGACTTCAGGAAGTATACTGCATTTACCAT
ACCTAGTATAAACAATGAGACACCAGGGATTAGATATCAGTACAATGTGCTTCCA
CAGGGATGGAAAGGATCACCAGCAATATTCCAAAGTAGCATGACAAAAATCTTAG
AGCCTTTTAGAAAACAAAATCCAGACATAGTTATCTATCAATACATGGATGATTTG
TATGTAGGATCTGACTTAGAAATAGGGCAGCATAGAACAAAAATAGAGGAGCTGA
GACAACATCTGTTGAGGTGGGGACTTACCACACCAGACAAAAAACATCAGAAAGA
ACCTCCATTCCTTTGGATGGGTTATGAACTCCATCCTGATAAATGGACAGTACAGC
CTATAGTGCTGCCAGAAAAAGACAGCTGGACTGTCAATGACATACAGAAGTTAGT
GGGGAAATTGAATTGGGCAAGTCAGATTTACCCAGGGATTAAAGTAAGGCAATTA
TGTAAACTCCTTAGA

FIGURE 2

Sequence of HIV-1 HXB2 strain polymerase gene region 2 (3400-4650 bp).

Sense orientation

GGAACCAAAGCACTAACAGAAGTAATACCACTAACAGAAGAAGCAGAGCTAG
AACTGGCAGAAAACAGAGAGATTCTAAAAGAACCAGTACATGGAGTGTATTAT
GACCCATCAAAAGACTTAATAGCAGAAATACAGAAGCAGGGGCAAGGCCAAT
GGACATATCAAATTTATCAAGAGCCATTTAAAAATCTGAAAACAGGAAAATAT
GCAAGAATGAGGGGTGCCCACACTAATGATGTAAAACAATTAACAGAGGCAG
TGCAAAAAATAACCACAGAAAGCATAGTAATATGGGGAAAGACTCCTAAATTT
AAACTGCCCATACAAAAGGAAACATGGGAAACATGGTGGACAGAGTATTGGC
AAGCCACCTGGATTCCTGAGTGGGAGTTTGTTAATACCCCTCCCTTAGTGAAAT
TATGGTACCAGTTAGAGAAAGAACCCATAGTAGGAGCAGAAACCTTCTATGTA
GATGGGGCAGCTAACAGGGAGACTAAATTAGGAAAAGCAGGATATGTTACTA
ATAGAGGAAGACAAAAAGTTGTCACCCTAACTGACACAACAAATCAGAAGAC
TGAGTTACAAGCAATTTATCTAGCTTTGCAGGATTCGGGATTAGAAGTAAACAT
AGTAACAGACTCACAATATGCATTAGGAATCATTCAAGCACAACCAGATCAAA
GTGAATCAGAGTTAGTCAATCAAATAATAGAGCAGTTAATAAAAAGGAAAA
GGTCTATCTGGCATGGGTACCAGCACACAAAGGAATTGGAGGAAATGAACAA
GTAGATAAATTAGTCAGTGCTGGAATCAGGAAAGTACTATTTTTAGATGGAAT
AGATAAGGCCCAAGATGAACATGAGAAATATCACAGTAATTGGAGAGCAATG
GCTAGTGATTTTAACCTGCCACCTGTAGTAGCAAAAGAAATAGTAGCCAGCTG
TGATAAATGTCAGCTAAAAGGAGAAGCCATGCATGGACAAGTAGACTGTAGTC
CAGGAATATGGCAACTAGATTGTACACATTTAGAAGGAAAAGTTATCCTGGTA
GCAGTTCATGTAGCCAGTGGATATATAGAAGCAGAAGTTATTCCAGCAGAAAC
AGGGCAGGAAACAGCATATTTTCTTTTAAAATTAGCAGGAAGATGGCCAGTAA
AAACAATACATACTGACAATGGCAGCAATTTCACCGGTGCTACGGTTAGGGCC
GCCTGTTGGTGGGCGGGAATCAAGCAGGAATTTGGAAT

FIGURE 3

Sequence of the HIV-1 HXB2 strain envelope gene region (6615-8053)

Sense orientation:

CACTGATTTGAAGAATGATACTAATACCAATAGTAGTAGCGGGAGAATGATAA
TGGAGAAAGGAGAGATAAAAAACTGCTCTTTCAATATCAGCACAAGCATAAGA
GGTAAGGTGCAGAAAGAATATGCATTTTTTTATAAACTTGATATAATACCAATA
GATAATGATACTACCAGCTATAGCTTGACAAGTTGTAACACCTCAGTCATTACA
CAGGCCTGTCCAAAGGTATCCTTTGAGCCAATTCCCATACATTATTGTGCCCCG
GCTGGTTTTGCGATTCTAAAATGTAATAATAAGACGTTCAATGGAACAGGACC
ATGTACAAATGTCAGCACAGTACAATGTACACATGGAATTAGGCCAGTAGTAT
CAACTCAACTGCTGTTAAATGGCAGTCTAGCAGAAGAAGAGGTAGTAATTAGA
TCTGTCAATTTCACGGACAATGCTAAAACCATAATAGTACAGCTGAACACATCT
GTAGAAATTAATTGTACAAGACCCAACAACAATACAAGAAAAGAATCCGTAT
CCAGAGAGGACCAGGGAGAGCATTTGTTACAATAGGAAAAATAGGAAATATG
AGACAAGCACATTGTAACATTAGTAGAGCAAAATGGAATAACACTTTAAAACA
GATAGATAGCAAATTAAGAGAACAATTCGGAAATAATAAAACAATAATCTTTA
AGCAATCCTCAGGAGGGGACCCAGAAATTGTAACGCACAGTTTTAATTGTGGA
GGGGAATTTTTCTACTGTAATTCAACACAACTGTTTAATAGTACTTGGTTTAAT
AGTACTTGGAGTACTGAAGGGTCAAATAACACTGAAGGAAGTGACACAATCAC
CCTCCCATGCAGAATAAAACAAATTATAAACATGTGGCAGAAAGTAGGAAAA
GCAATGTATGCCCCTCCCATCAGTGGACAAATTAGATGTTCATCAAATATTACA
GGGCTGCTATTAACAAGAGATGGTGGTAATAGCAACAATGAGTCCGAGATCTT
CAGACTTGGAGGAGGAGATATGAGGGACAATTGGAGAAGTGAATTATATAAA
TATAAAGTAGTAAAAATTGAACCATTAGGAGTAGCACCCACCAAGGCAAAGA
GAAGAGTGGTGCAGAGAGAAAAAAGAGCAGTGGGAATAGGAGCTTTGTTCCT
TGGGTTCTTGGGAGCAGCAGGAAGCACTATGGGCGCAGCCTCAATGACGCTGA
CGGTACAGGCCAGACAATTATTGTCTGGTATAGTGCAGCAGCAGAACAATTTG
CTGAGGGCTATTGAGGCGCAACAGCATCTGTTGCAACTCACAGTCTGGGGCAT
CAAGCAGCTCCAAGCAAGAATCCTAGCTGTGGAAAGATACCTAAAGGATCAAC
AGCTCCTAG

FIGURE 5
Antisense vectors
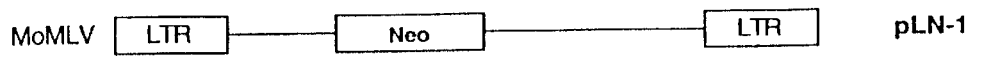
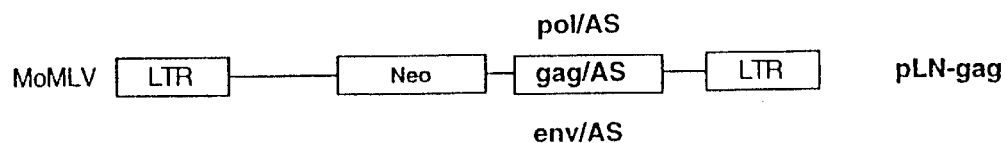
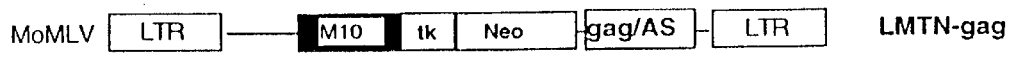
5' end of the HIV genome
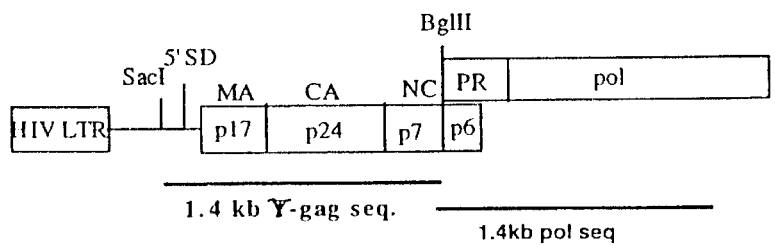

FIGURE 12
HIV-1 challenge of pol1-env antisense combination constructs
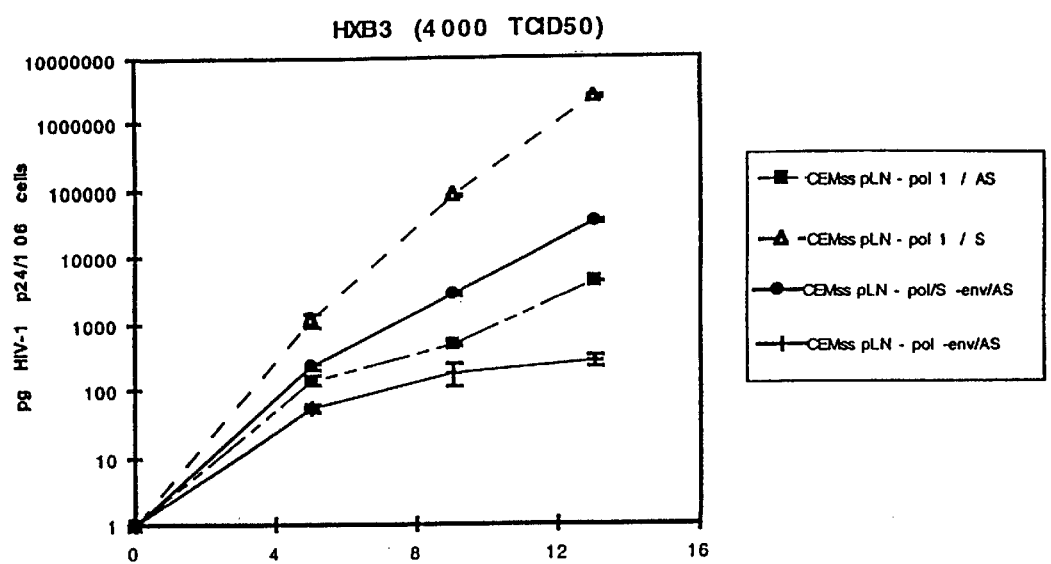
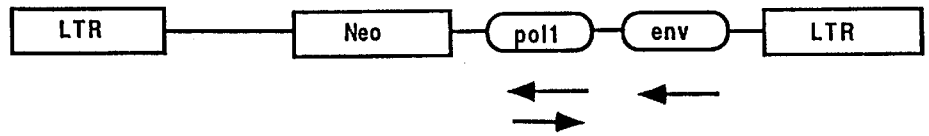

FIGURE 15
A
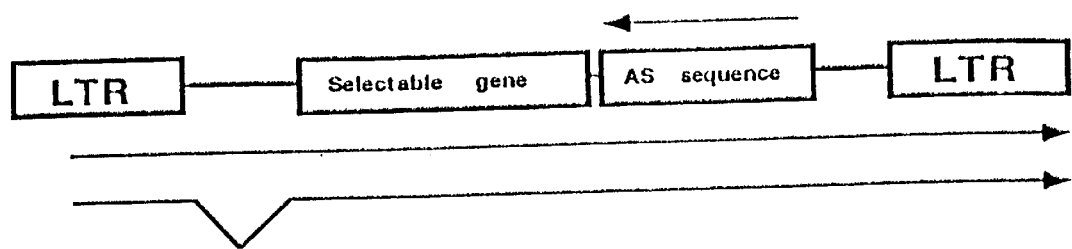
B
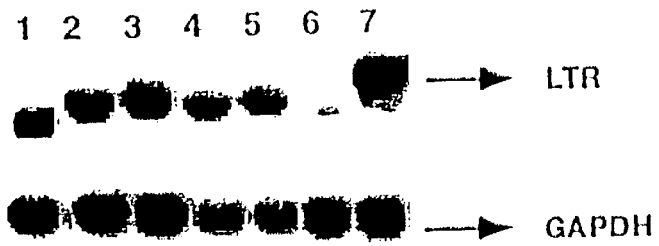

FIGURE 18
A
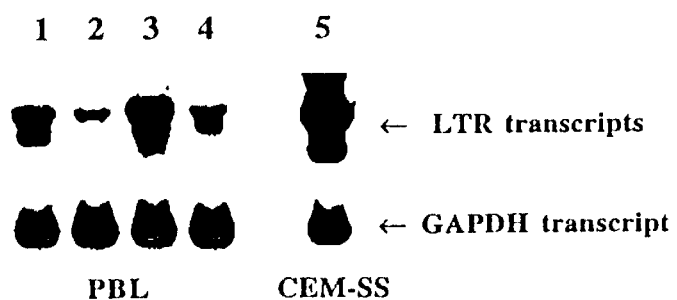
B
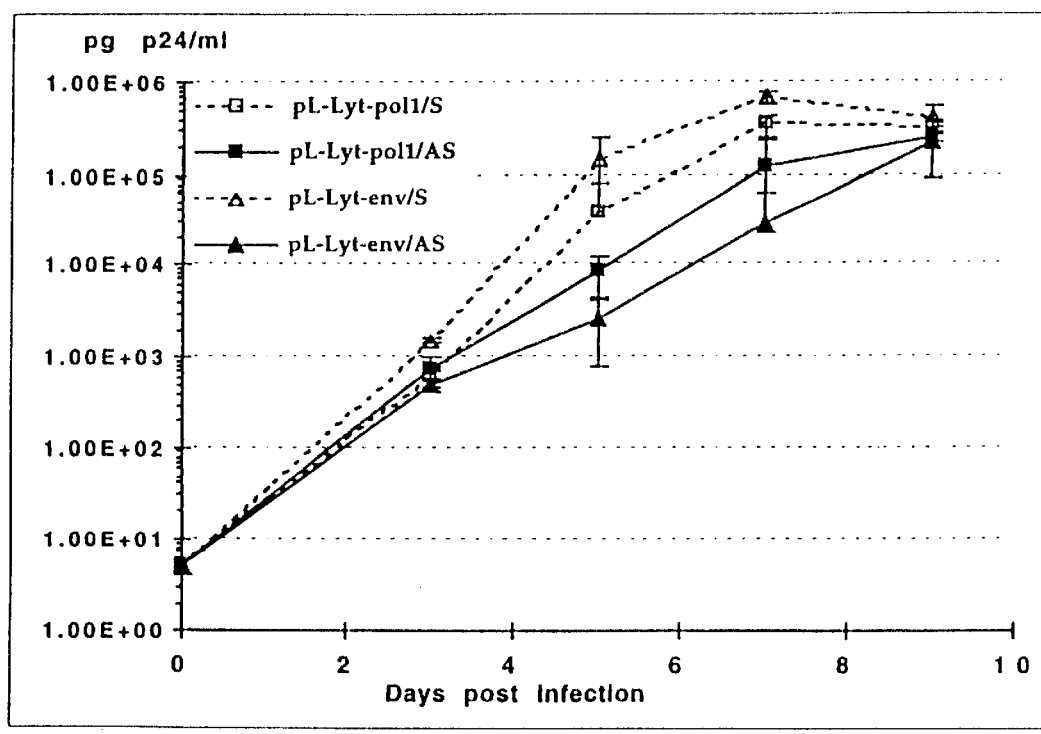

INHIBITION OF HIV-1 REPLICATION BY ANTISENSE RNA EXPRESSION

CROSS-REFERENCES TO RELATED APPLICATIONS

This application is a 371 of PCT/EP97/02952, filed Jun. 6, 1997 which claims priority to U.S. Provisional Application No. 60/019232, filed Jun. 6,1996.

This invention relates to inhibition of HIV-1 replication using antisense RNA expression.

BACKGROUND OF THE INVENTION

1. Field of the Invention

2. Description of the Related Art

HIV-1 infection is believed to be the primary cause of Acquired Immunodeficiency Syndrome (AIDS). HIV-1 is a retrovirus having a genome comprised of two copies of full length RNA. Without intending to be bound by a particular theory, it is hypothesized that the replication of the virus in the CD4+ host cell occurs as follows. When the host cell is infected, the viral genomic RNA is transcribed by reverse trascriptase into double stranded DNA. This double stranded DNA is then integrated into the host cell's chromosome(s). When this double stranded DNA is integrated iinto the genetic material of the host cell, it is called a provirus. Following activation of the host cell, the provirus is transcribed into RNA in two distinct phases. In the early phase of infection, RNA transcripts of the provirus produced in the nucleus are converted into multiple copies of short sequences by cellular splicing enzymes. These short RNA transcripts encode genes for proteins, e.g., tat, which regulate the further transcription, and rev, which is though to mediate the transition into the late phase transcription. This early phase dominates for about 24 hours. About 24 hours after activation of the cell, the transcription moves into the late phase. In late phase transcription, long unspliced RNA transcripts of about 9,200 bases and medium-length single-spliced transcripts of about 4,500 bases move out of the nucleus and into the cytoplasm. These unspliced and single-spliced transcripts encode the structural and enyzmatic proteins of the virus. These unspliced and single-spliced transcripts include, inter alia, the following regions: gag, which encodes the viral core proteins; pol, which encodes various enzymes; and env, which encodes the two envelope proteins. FIG. 4 depicts the HIV-1 genomic structure. It will be noted that there is some overlap in the genes, because certain genes share some base sequences.

The unspliced and single-spliced transcripts are then further spliced, and the resulting mRNA is translated to produce the proteins necessary to make a new virus. The gag and pol regions are translated to produce the polyproteins gag and gag-pol, which are then cleaved by protease to form the mature proteins found in the virus. The env is spliced to generate a subgenomic messenger which encodes for the env polyproteins, which is likewise cleaved to produce the mature envelope proteins. Two strands of the viral RNA are then packaged into a core and surrounded with capsid protein, and the resulting virus is released from the cell together with a portion of the cell membrane.

Various antisense strategies to inhibit HIV-1 infection have been tried, including the use of trans-domninant proteins (Bevec, D., et al. 1992. Inhibition of human immunodeficiency virus type 1 replication in human T cells by retroviral-mediated gene transfer of a dominant-negative rev trans-activator. Proc. Natl. Acad. Sci. USA 89:9870–9874 and Trono, D., et al. 1989. HIV-1 gag mutants can dominantly interfere with the replication of the wild-type virus. Cell 59:113–120), single chain antibodies (Levy-Mintz, P., et al. 1996. Intracellular expression of single-chain variable fragments to inhibit early stages of the viral life cycle by targeting human immunodeficiency virus type 1 integrase. J. Virol. 70:8821–8832.), antisense RNAs (Chatterjee, S., et al. 1992. Dual-target inhibition of HIV-1 in vitro by means of adeno-associated virus antisense vector. Science 258:1485–1488., Choli, H., et al. 1994. Inhibition of HIV-1 multiplication in a human CD4+ lymphocytic cell line expressing antisense and sense RNA molecules containing HIV-1 packaging signal and rev response element(s). Antisense Res. and Dev. 4:19–29, Joshi, S., et al. 1991. Inhibition of human immunodeficiency virus type 1 multiplication by antisense and sense RNA expression. J. Virol. 65:5524–5530, Kim, J. H., et al., 1996. Inhibition of HIV replication by sense and antisense Rev Response Elements in HIV-based retroviral vectors. J. Acquir. Immune Defic. Syndr. 12:343–351, Meyer, J., et al., 1993. Inhibition of HIV-1 replication by high-copy-number vector expressing antisense RNA for reverse transcriptase. Gene 129:263–268, Renneisen, K., et al 1990. Inhibition of expression of human immunodeficiency virus-1 in vitro by antibody-targeted liposomes containing antisense RNA to the env region. J. Biol. Chem. 265:16337–16342 and Rhodes, A., et al. 1990. Inhibition of human immunodeficiency virus replication in cell culture by endogenously synthesized antisense RNA. J. Gen. Virol. 71:1965–1974), RNA decoys (Lee, T., et al. 1994. Inhibition of human immunodeficiency virus type 1 in human T cells by a potent Rev-response element decoy consisting of the 13-nucleotide minimal Rev-binding domain. J. Virol. 68:8254–8264 and Sullenger, B. A., et al 1990. Overexpression of TAR sequences renders cells resistant to human immunodeficiency virus replication. Cell 63:601–608), and ribozymes (Ojwang, J. O., et al 1992. Inhibition of human immunodeficiency virus type 1 expression by a hairpin ribozyme. Proc. Natl. Acad. Sci. USA. 89:10802–10806 and Zhou C., I. Bahner, et al 1994. Inhibition of HIV-1 in human T lymphocytes by retrovirally transduced anti-tat and rev hammerhead ribozymes. Gene. 149:33–39).

The trans-dominant HIV-1 protein RevM10 was first evaluated in a clinical trial using genetically modified peripheral blood lymphocytes (Woffendin, C et al. 1996. Expression of a protective gene prolongs survival of T cells in human immunodeficiency virus infected patients. Proc. Natl. Acad. Sci. USA. 93:2889–2894), although recently a ribozyme (Leavitt, M. C., et al 1996. Ex vivo transduction and expansion of CD4+ lymphocytes from HIV+ donors: prelude to a ribozyme gene therapy trial. Gene Ther. 3:599–606) and a transdominant Rev and antisense TAR based (Morgan R. A et al 1996. Clinical protocol: Gene therapy for AIDS using retroviral mediated gene transfer to deliver HIV-1 antisense TAR and transdominant Rev protein genes to syngeneic lymphocytes in HIV-1 infected identical twins. Hum. Gene Ther. 7:1281–1306.) approach have received RAC and FDA approval.

Intracellular expression of antisense RNAs offers an attractive, alternative gene therapy approach to inhibit HIV-1 replication. Antisense RNAs have been described as very specific and efficient inhibitors in both prokaryotic and eukaryotic systems . Viral replication has been successfully inhibited by addition of in vitro synthesized antisense oligonucleotides or intracellularly expressed antisense RNAs . Inhibition of HIV-1 replication has been shown previously using antisense RNAs targeted against several viral regulatory (Chatterjee et al 1992, Joshi et al 1991, Kim et al 1996, Sczakiel, G. et al 1991. Inhibition of human immunodeficiency virus type 1 replication in human T cells stably expressing antisense RNA. J. Virol. 65:468472 and Sczakiel, G et al 1992. Tat- and Rev-directed antisense RNA expression inhibits and abolishes replication of human immunodeficiency virus type 1: a temporal analyses. J. Virol. 66:5576–5581) and structural gene products (Choli et al 1994, Gyotoky, et al 1991, Meyer et al 1993 and Rhodes et al 1990). A few reports described long antisense sequences expressed either intracellularly using retroviral vectors (Choli et al 1994, Gyotoky, et al 1991 and Rhodes et al 1990) or using antibody-targeted liposomal delivery (Renneisen et al). The different inhibition levels observed in these reports may reflect variation in antisense RNA expression levels, or secondary and tertiary RNA structures, which can influence the hybridization kinetics between two complementary RNAs (Sczakiel, G., M. Homann, and K. Rittner. 1993 Computer-aided search for effective antisense RNA target sequences of the human immunodeficiency virus type 1. Antisense Res. and Dev. 3:45–52), influencing the biological activity.

Generally, these efforts have targeted the early phase transcription (e.g., tat or rev genes) or have targeted RNA processing or initiation of translation in the late phase. Shorter antisense sequences have been favored due to the perceived risk of the antisense sequence folding to form a secondary structure with itself. To date, these efforts have not met with significant success.

It is now surprisingly discovered that the best target for antisense therapy is the full length or single-spliced RNA transcript. Antisense sequences which bind to multiple-spliced transcripts for a gene are less effective, probably because binding to the smaller transcripts results in fewer antisense molecules being available for the binding to the full length or single spliced transcripts. Moreover, longer sequences directed to the full length transcript (e.g., sequences greater than 600 base pairs, preferably greater than 1000 base pairs) are surprisingly effective and, contrary to the suggestion in the art, do not appear to form undesirable secondary structures.

SUMMARY OF THE INVENTION

Hereinafter we present the results of the antiviral activity of sequences complementary to the pol, vif, env genes and 3'LTR in HIV-1 infection experiments using a human CD4$^+$T cell line (CEM-SS) and peripheral CD4$^+$T lymphocytes (PBLs). Retroviral vectors are constructed expressing chimeric RNAs containing 1,100–1,400 nt long complementary HIV-1 sequences. The most efficient inhibition of HIV-1 replication is observed with an antisense sequence complementary to the HIV-1 env gene both in the CEM-SS cell line and in PBLs. This strong antiviral effect is further demonstrated in high inoculation dose infection experiments where reduction of the HIV-1 mRNAs correlates with low level of Gag and Tat protein production indicating that antisense RNA acts early during HIV-1 replication. Comparing the anti-HIV-1 efficacy of the antisense RNAs to the well documented (Bevec, D.,et al. 1992. Inhibition of human immunodeficiency virus type 1 replication in human T cells by retroviral-mediated gene transfer of a dominant-negative rev trans-activator. Proc. Natl. Acad. Sci. USA 89:9870–9874, Escaich, S., et al 1995. RevM10-mediated inhibition of HIV-1 replication in chronically infected T cells. Hum. Gene Ther. 6:625–634, Malim, M. H., et al. 1992. Stable expression of transdominant rev protein in human T cells inhibits human immunodeficiency virus replication. J. Exp. Med. 176:1197–1201 and Nabel, G. J., et al. 1995. A molecular genetic intervention for AIDS—effects of a transdominant negative form of Rev. Hum. Gene Ther. 5:79–92) trans-dominant RevM10 protein demonstrates the potency of the antisense mediated inhibition of HIV-1 replication.

It has further been discovered that antisense sequences to the gag, env, and pol, especially the env and pol portions of the full length transcript are particularly effective.

The above mentioned antisense constructs are particularly useful for providing gene therapy to patients suffering from HIV-1 infection, e.g., by transducing the HIV-1-susceptable cells of such patients, e.g., CD4+ cells or cells which are progenitors of CD4+ cells, e.g., hematopoietic stem cells (for example CD34+/Thy-1+cells), with the antisense constructs of the invention, so that the transduced cells and their progeny are resistant to HIV-1 infection.

The antisense constructs of the invention are suitably prepared by incorporating a wild-type HIV-1 gene or gene fragment into a vector in reverse orientation with respect to its promotor so that when the gene is incorporated into the genome of the host cell and transcribed, the opposite strand of the DNA is transcribed, producing a messenger RNA transcript which is complementary to the mRNA from the wild-type gene or gene fragment and will anneal with it to form an inactive RNA-RNA duplex, which is subject to degradation by cellular RNases.

Transduction of the HIV-1 susceptable cells using the antisense vectors can be carried out in vivo or ex vivo, but is suitably carried out ex vivo, by removing blood from the patient, selecting the target cells, inoculating them with a vector containing the antisense construct of the invention, and reintroducing the transduced cells into the body. By natural selection, the transduced HIV-1 resistant cells will replace the native HIV-1 susceptible cells, thereby enabling the patient to overcome the infection and regain immunocompetence. Alternatively, the patient receives non-autologous CD4+ cells or progenitors of CD4+ cells from a compatable donor which cells have been transduced with the antisense construct of the invention.

The invention thus provides:

1. A nucleic acid sequence which, when stably integrated into a human cell, is capable of generating mRNA which anneals e.g., under in vivo conditions, with a mRNA transcript from an HIV-1 provirus encoding env, env and pol or env, pol and gag and which is at least 0.6 kb, preferably at least 1 kb in length, most preferably 1–2 kb, e.g. from 1.1 to 1.5 kb; and which is selected from:

(i) a sequence which is antisense to the 1.4 kb fragment from the Apa1 cleavage site at ca. base 2004 of an HIV-1 provirus to the Pflm 1 cleavage site ca. base 3400 of an HIV-1 provirus, e.g. which is antisense to the sequence in FIG. 1 (SEQ. ID. NO. 1);

(ii) a sequence which is antisense to the 1.2 kb fragment from the Pflim 1 cleavage site ca. base 3400 of an HIV-1 provirus to the EcoR1 cleavage site ca. base 4646 of an HIV-1 provirus, e.g. which is antisense to the sequence in FIG. 2 (SEQ. ID. NO. 2);

(iii) a sequence which is antisense to the 1.3 kb fragment from the ApaL1 cleavage site ca. base 6615 of an HIV-1 provirus to the Bsm1 cleavage site ca. base 8053 of an HIV-1 provirus, e.g., which is antisense to the sequence in FIG. 3 (SEQ. ID. NO.3); and (iv) a sequence which is at least 80%, preferably at least 90%, more preferably at least 95%, most preferably at least 99%, homologous to a sequence according to (i), (ii), or (iii) and which is capable of generating mRNA which annealss to the same mRNA transcript as that hybridizing to mRNA generated by (i), (ii), or (iii).

It is understood that the nucleic acid described in 1 above will be in RNA for when in a retroviral vector and will be converted to DNA upon incorporation of the provirus into the target cell. It is intended that both the RNA and DNA forms of the constructs are included within the scope of the invention.

The invention further provides

2. A vector comprising an antisense sequence according to 1 above.

The vector may be any vector capable of transducing a human hematopoietic cell, for example, an ecotropic, xenotropic, amphotropic or pseudotyped retroviral vector, an adeno-associated virus (AAV) vector, or an adenovirus (AV) vector. Preferably, the vector is a retroviral vector, preferably a vector characterized in that it has a long terminal repeat sequence (LTR), e.g., a retroviral vector derived from the Moloney murine leukemia virus (MoMLV), myeloproliferative sarcoma virus (MPSV), or murine embryonic stem cell virus (MESV), or for example, a vector from the pLN series described in Miller and Rosman (1989) BioTechniques 7, pp. 980–986. The antisense sequence replaces the retroviral gag, pol and/or env sequences. The promotor controlling expression of the antisense may be a strong viral promoter, for example MoMLV LTR.

The range of host cells that may be infected by a retrovirus or retroviral vector is generally determined by the viral env protein. The recombinant virus generated from a packaging cell can be used to infect virtually any cell type recognized by the env protein provided by the packaging cell. Infection results in the integration of the viral genome into the transduced cell and the consequent stable expression of the foreign gene product. The efficiency of infection is also related to the level of expression of the receptor on the target cell. In general, murine ecotropic env of MoMLV allows infection of rodent cells, whereas amphotropic env allows infection of rodent, avian and some primate cells, including human cells. Xenotropic vector systems utilize murine xenotropic env, and also allow infection of human cells. The host range of retroviral vectors may be altered by substituting the env protein of the base virus with that of a second virus. The resulting, "pseudotyped" virus has the host range of the virus donating the envelope protein and expressed by the packaging cell line. For example, the G-glycoprotein from vesicular stomatitis virus (VSV-G) may be substituted for the MMLV env protein, thereby broadening the host range. Preferably the vector and packaging cell line of the present invention are adapted to be suitable for transduction of human cells. Preferably, the vector is an amphotropic retroviral vector, for example, a vector as described in the examples below.

Optionally, the vector may contain more than one antisense sequence according to 1 above, e.g., two different antisense sequences, for example to pol and env, as described in the examples below.

Preferably, the construct lacks the retroviral gag, pol and/or env sequences, so that the gag, pol and env functions must be provided in trans by a packaging cell line. Thus, when the vector construct is introduced into the packaging cell, the gag-pol and env proteins produced by the cell assemble with the vector RNA to produce replication-defective or transducing virions that are secreted into the culture medium. The virus thus produced can infect and integrate into the DNA of the target cell, but generally will not produce infectious viral particles since it is lacking essential viral sequences. The packaging cell line is preferably transfected with separate plasmids encoding gag-pol and env, so that multiple recombination events are necessary before a replication-competent retrovirus (RCR) can be produced. Suitable retroviral vector packaging cell lines include those based on the murine NIH/3T3 cell line and include PA317 (Miller & Buttimore (1986) Mol. Cell Biol. 6:2895; Miller & Rosman (1989) Bio Techniques 7:980), CRIP (Danos & Mulligan (1988) Proc. Natl Acad Sci USA 85:6460), and gp+am12 (Markowitz et al. (1988) Virology 167:400); and also cell lines based on human 293 cells or monkey COS cells, for example ProPak A packaging cells, e.g., as described in Pear et al. (1993) Proc. Natl. Acad. Sci. USA 90:8392–8396; Rigg et al., (1996) Virology 218; Finer, et al. (1994) Blood 83:43–50; Landau, et al. (1992) J. Virol. 66:5110–5113. Retroviral vector DNA can be introduced into packaging cells either by stable or transient transfection to produce retroviral vector particles.

The antisense constructs of the invention have the further advantage that they will not interfere with expression of HIV inhibitory proteins, e.g., transdominant mutant proteins corresponding to the early phase short MRNA transcripts, for example mutants of tat or rev. Expression of such transdominant mutant proteins is useful in treating HIV infection because the mutant proteins interfere with the function of the wild-type HIV proteins and so inhibit HIV replication. A transdominant mutant protein of particular interest is RevM10, the use of which is described e.g., in Escaich, et al. Hum. Gene Ther. (1995) 6:625–634, and in WO 90/14427. Previously, co-expression of HIV antisense and transdominant mutant proteins was considered impractical because it was expected that the antisense would interfere with expression of the mutant protein. Using the antisense constructs of the invention, co-expression of the antisense with the transdominant mutant protein is not only feasible but provides a synergistic inhibition of the HIV by interfering with the virus at different stages of its replication cycle.

Thus the invention provides in a further embodiment:

3. A retroviral vector according to 2 above (i.e., comprising an antisense sequence according to 1 above) and further comprising a gene for an HIV-1 inhibitory protein, e.g., a gene for a transdominant mutant form of tat or rev, especially the gene for RevM10.

Packaging cell lines comprising the vectors according to 2 or 3 above, e.g, as described above, are also within the scope of the invention.

The invention also provides in a further embodiment:

4. A cellular composition comprising at least one human hematopoietic cell (e.g. CD4+ cell or progenitor of CD4+ cells, e.g., a stem cell, e.g., a CD34+/Thy-1+ cell) stably transduced with an antisense sequence according to 1 above and optionally additionally transduced with a gene for a transdominant mutant form of tat or rev, especially RevM10, e.g., transduced with a vector according to 2 or 3, supra, e.g., for use in a method according to 5 below;

The invention also provides in a further embodiment:

5. A method for treatment of HIV-1 infection in a subject in need thereof comprising isolating hematopoietic cells (e.g. CD4+ cells or progenitors of CD4+ cells, e.g., stem cells, e.g., CD34+/Thy-1+ cells) from said patient;

transducing said cells with an antisense sequence according to 1 above, and optionally additionally or simultaneously transducing said cells with a gene for an HIV-1 inhibiting transdominant mutant form of tat or rev, especially RevM10, e.g., transducing said cells with a vector according to 2 or 3, supra; and reintroducing the transduced cells into the patient.

The invention also provides in a further embodiment:

6. The use of an antisense sequence according to 1 above or a vector according to 2 or 3 above in the manufacture of a cellular composition according to 4 above or in a method of treatment according to 5 above.

BRIEF DESCRIPTION OF THE DRAWINGS

FIG. 1 (SEQ ID NO: 1) depicts the sequence of HIV-1 HXB2 strain polymerase gene region 1 (2004-3400 bp) in sense orientation.

FIG. 2 (SEQ ID NO: 2) depicts the sequence of HIV-1 HXB2 strain polymerase gene region 2 (34004650 bp) in sense orientation.

FIG. 3 (SEQ ID NO: 3) depicts the sequence of HIV-1 HXB2 strain envelope gene region (6615-8053 bp) in sense orientation.

FIG. 5 depicts the schematic structure of antisense vectors of the examples. The parental vector pLN-1 is described in the publication of A. Dusty Miller and Guy J. Rosman (1989) BioTechniques 7. 980–986. The multicloning site 3' from the Neo gene is used to insert the antisense fragments. The parental vector for the combination vectors pLMTNL is described in: Escaich, S. Kalfoglu, C.; Plavec, I; et al. Human Gene Therapy 1995. 6. 625–634.

FIG. 12 depicts the pLN pol1/env antisense vectors, and the effectiveness of pol1 (S), pol1 (AS), pol1 (AS)/env(S), pol(AS)/env(AS) against HIV-1 challenge, the double antisense construct being the most effective.

FIG. 15. A. Structure of the retroviral vectors encoding the antisense sequences. Neo and Lyt2 are used as a selectable marker genes. The antisense sequence together with the marker gene is expressed from the MoMLV LTR promoter. The arrow indicates the antisense orientation of the inserted HIV-1 sequences. B. Northern blot analyses of the antisense RNA expression in transduced CEM-SS cells. The recombinant transcripts carrying the antisense sequences are detected using a Neo specific probe. The lower panel indicates the same blot hybridized with a GAPDH specific probe as a internal standard. Lane 1: pLN vector, lane 2: pLN-pol1/AS, lane 3: pLN-pol2/AS, lane 4:pLN-vif/AS, lane 5:pLN-env/AS, lane 6:pLN-3'LTR/AS, lane 7: pLN-pol12/AS vector respectively.

FIG. 18. Antisense RNA expression and inhibition of HIV-1 replication in transduced PBLs. A. Total cellular RNA is isolated from activated, CD4+ enriched PBLs transduced with pL-Lyt-pol1/AS, pL-Lyt2/pol1/S, pL-Lyt-env/AS, pL-Lyt2/env/S vectors and selected for Lyt2 expression. The antisense transcripts are analyzed on Northern blot using a radiolabeled Lyt2 specific probe. A GAPDH specific probe is used to monitor the amount of RNA loaded. Lane 1:pL-Lyt2-pol1/AS, Lane 2:pL-Lyt2-pol1/S, Lane 3: pL-Lyt2-env/AS, Lane 4: pL-Lyt-env/S, Lane 5:pL-Lyt2-pol1/AS. B. Transduced and CD4+ Lyt2+ selected PBLs are activated with allogenic feeder cells and infected with the clinical HIV-1 isolate JR-CSF. $5 \times 10^4$ cells are inoculated in triplicate, and p24 antigen production is determined.

DETAILED DESCRIPTION OF THE PREFERRED EMBODIMENTS

EXAMPLES

Example 1

Figure 4:
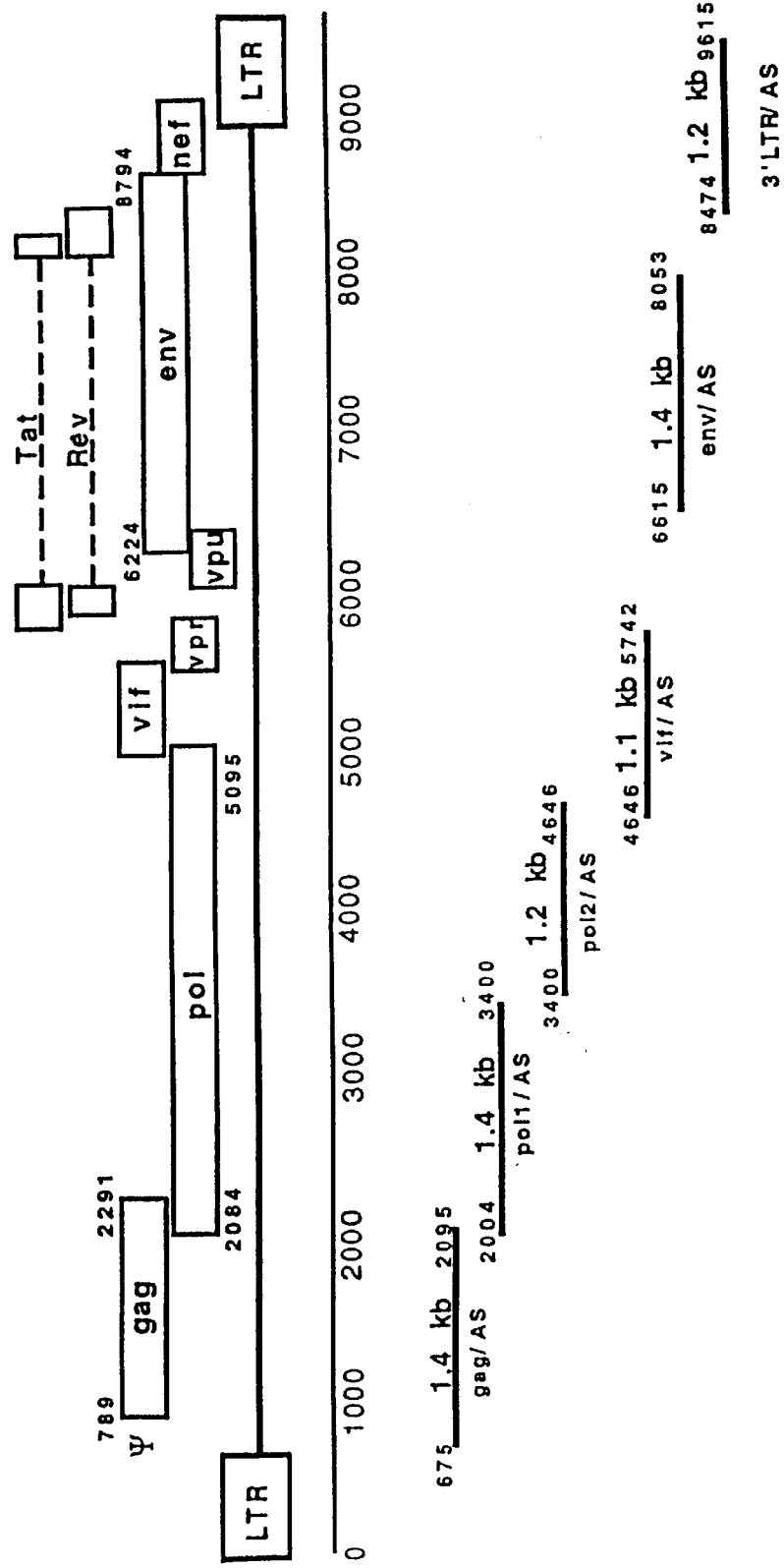
FIG. 4 depict the HIV-1 genomic structure. The position of antisense fragment used for vector construction is also shown. The position of the restriction endonuclease cleavage sites is indicated for each fragment.
Figure 6:
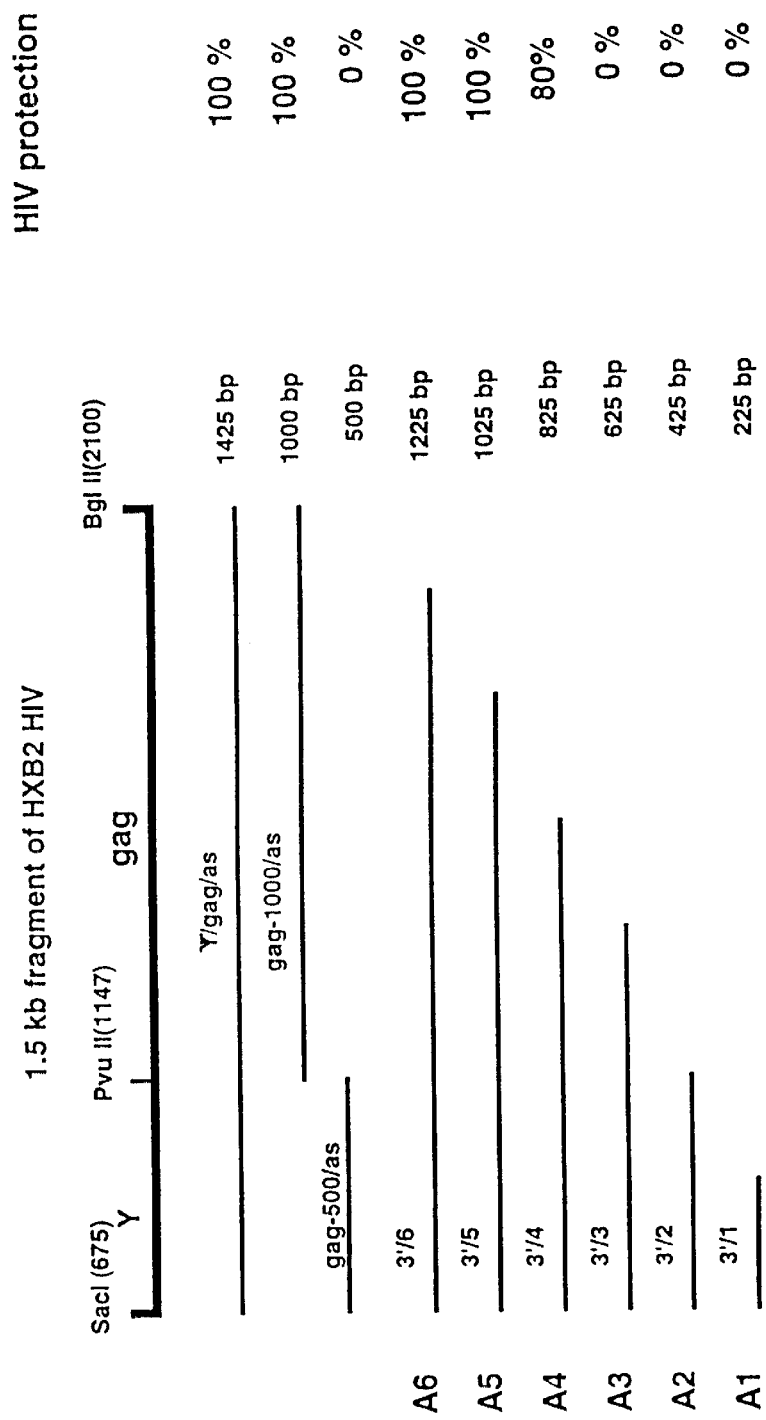
FIG. 6 depicts serial deletion of HIV gag sequence. Construction of the deletion fragments is described below. The 1.5 kb SacI-BglII psi-gag fragment (Ψ-gag) is used to generate the deletion construct either by PCR amplification or by restriction digest.
Figure 7:
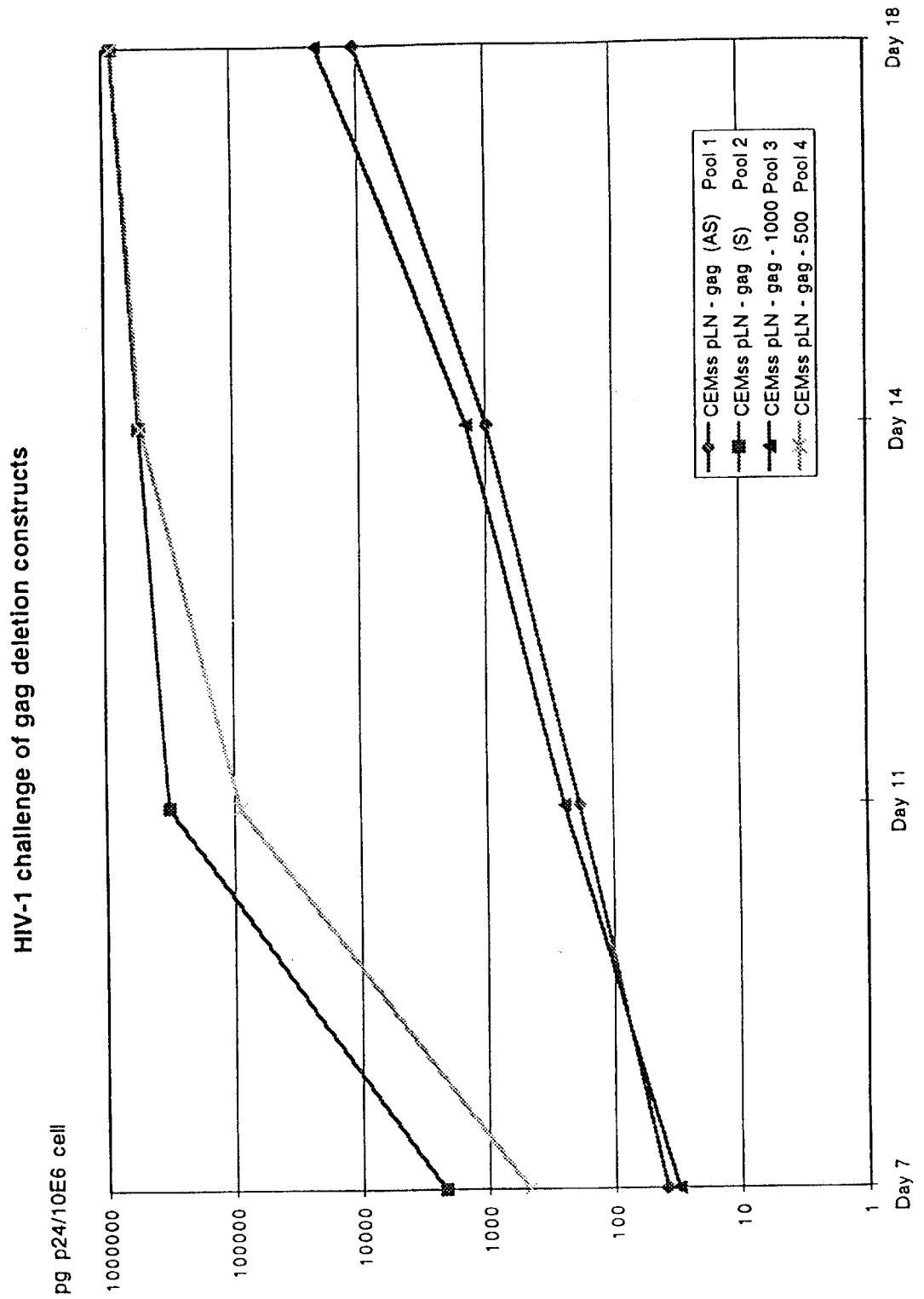
FIG. 7 depicts HIV challenge of deletion constructs. The pLN-gag (S) and pLN-gag (AS) construct correspond to the full length 1.5 kb psi-gag fragment in sense or antisense orientation respectively. The pLN-gag-500 is the 5' end of the above fragment corresponding mostly to the psi (packaging signal) sequence of the HIV-1. The pLN-gag-1000 construct corresponds to the gag region of the 1.5 kb fragment.
Figure 8:
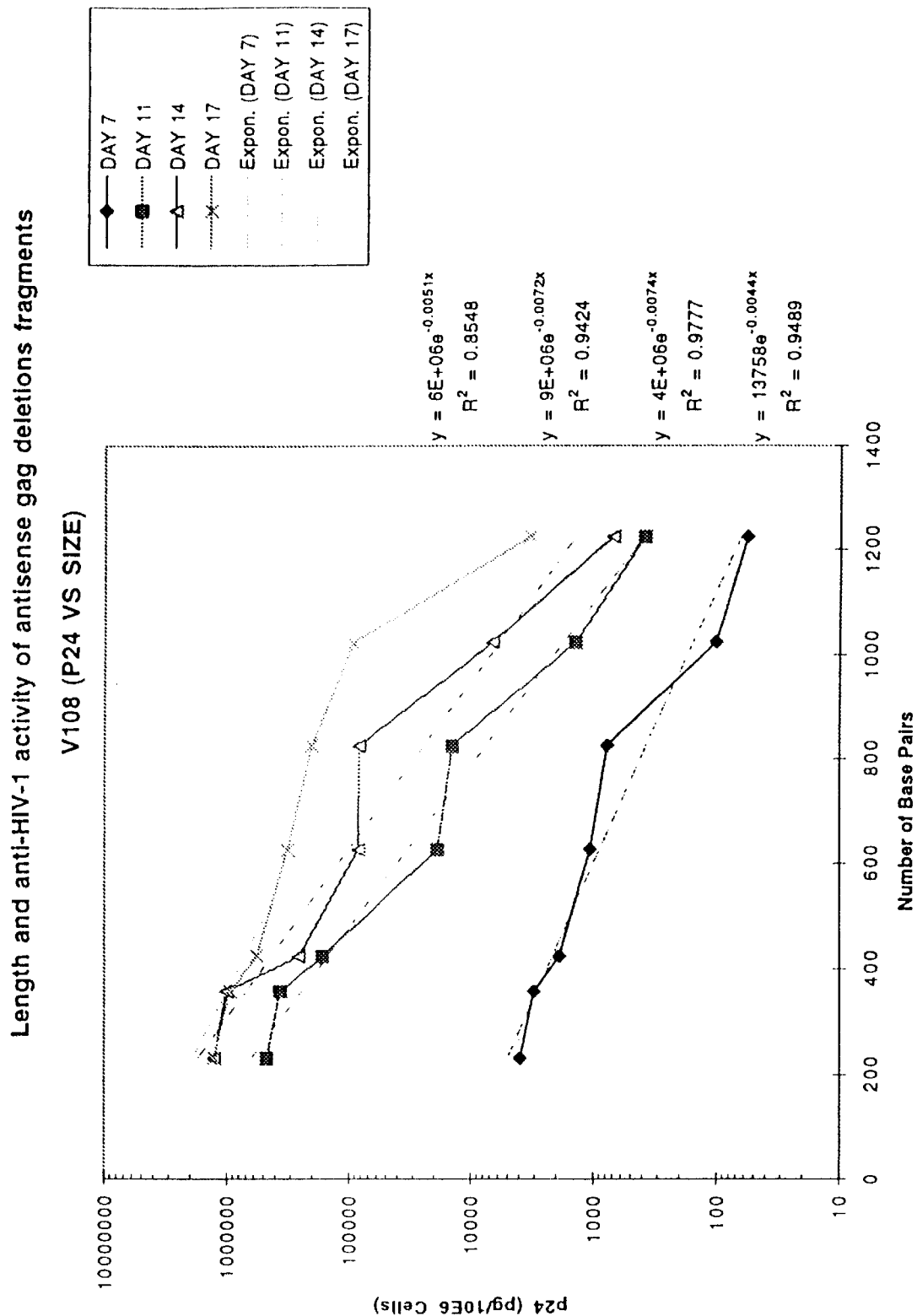
FIG. 8 depicts the anti-HIV-1 activity of antisense gag deletion fragments as a function of their length; correlation between size and anti-HIV-1 activity is shown on the graph. The p24 production (pg/10E6 cells) versus the length of the fragments in base pairs is plotted on the graph.
Figure 9:
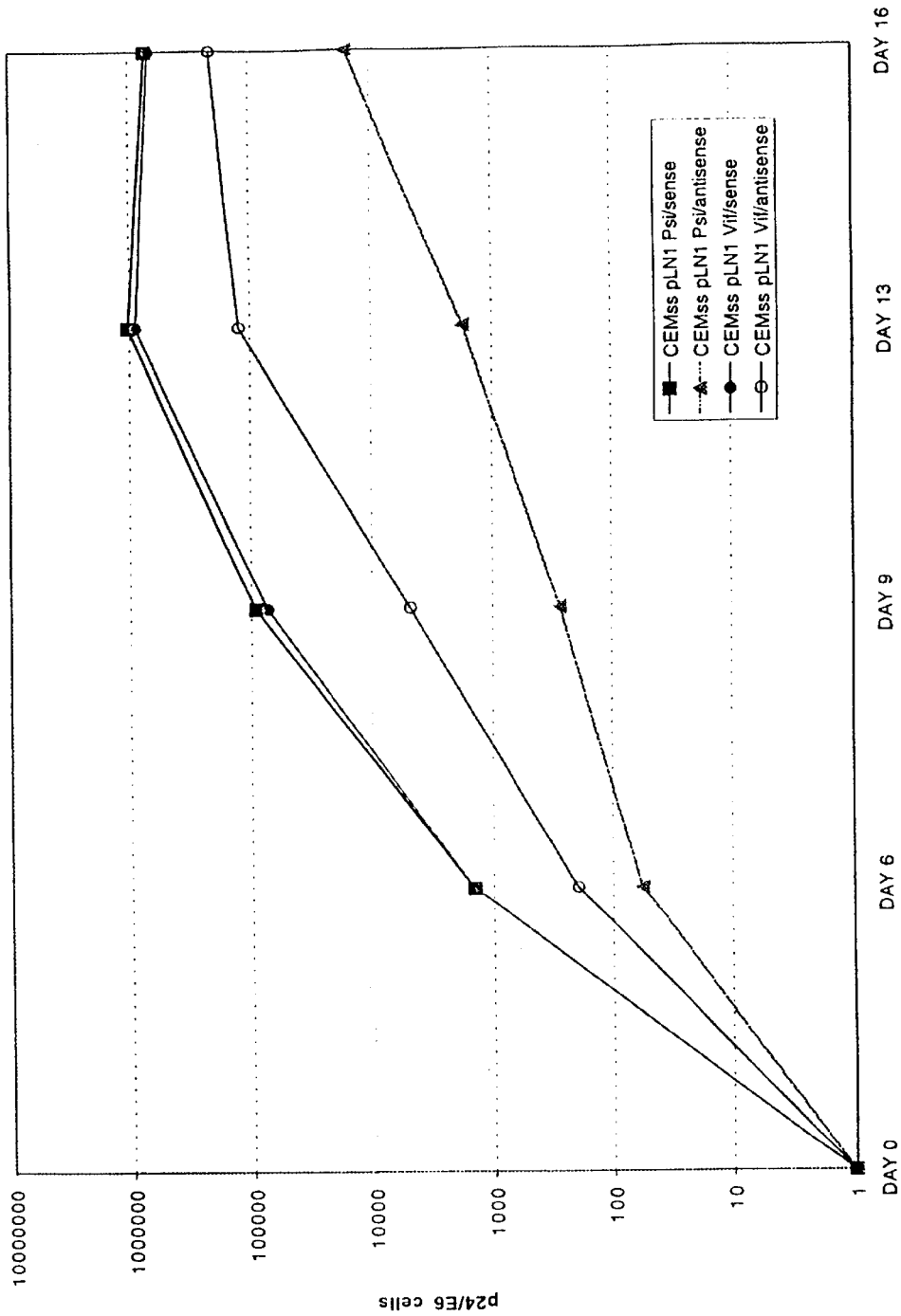
FIG. 9 depicts HIV-1 challenge of antisense gag and Vif constructs. The full length, 1.5 kb antisense gag (pLN1 Psi-sense and antisense) and the similar size Vif fragment (pLN1 Vif/sense and antisense) are compared.
Figure 10:
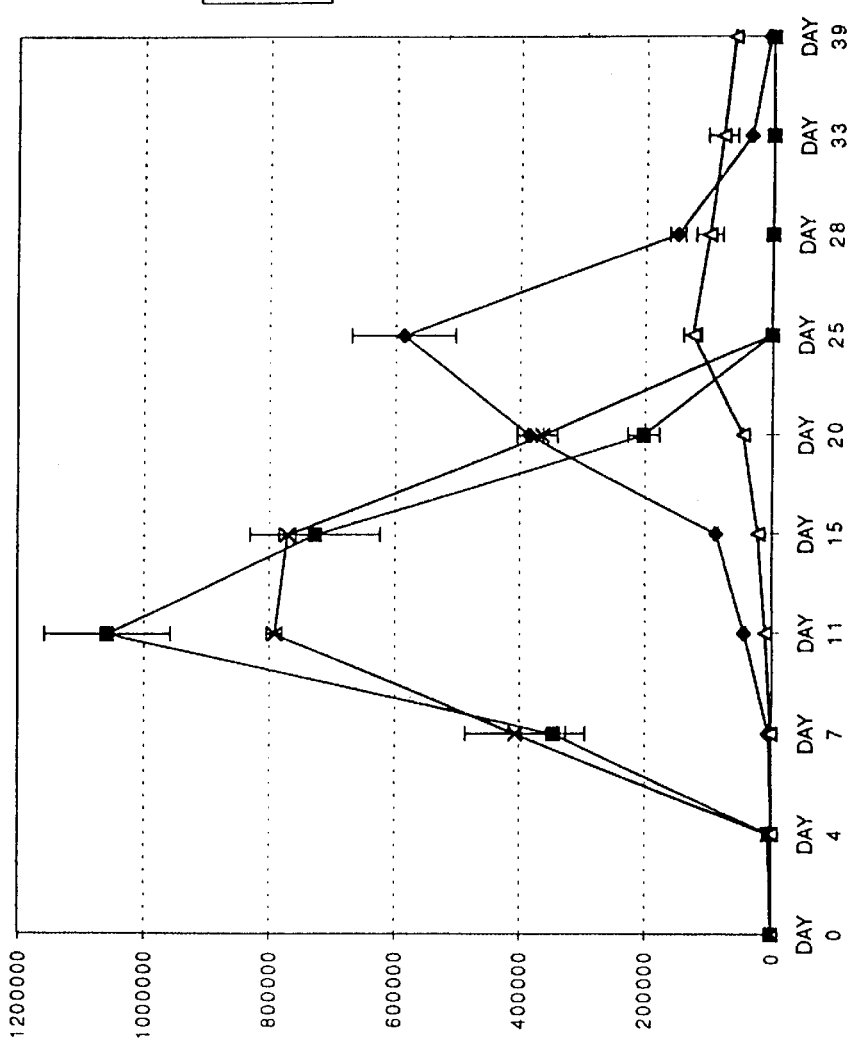
FIG. 10 depicts HIV-1 challenge of gag-pol/AS constructs with high dose of virus (40000 TCID50): The 1.5 kb psi-gag fragment (pLN-gag/AS and S) was compared with the pol-1 fragment (pLM-pol/AS and S).
Figure 11:
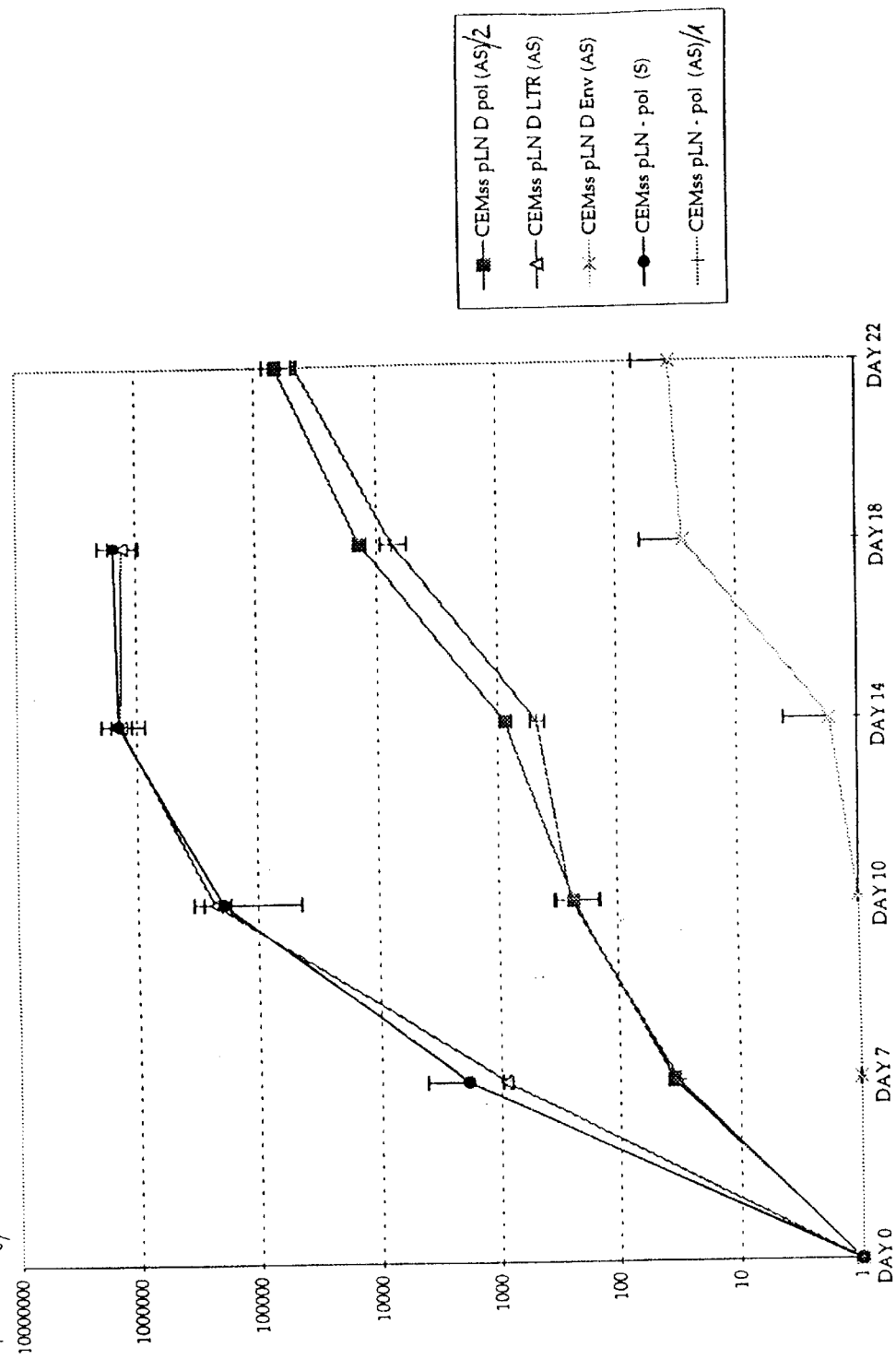
FIG. 11 depicts HIV-1 challenge of antisense pol, env and LTR constructs. CEMSS cells carrying the pol-1 fragment (pLN-pol (AS)/1 and (S)/1) the second antisense pol-2 (pLN Dpol (AS)/2) the envelope (pLN D Env (AS)) and the 3'LTR) pLN D LTR (AS)) fragments are challenged with 400 TCID HIV-1.
Figure 13:
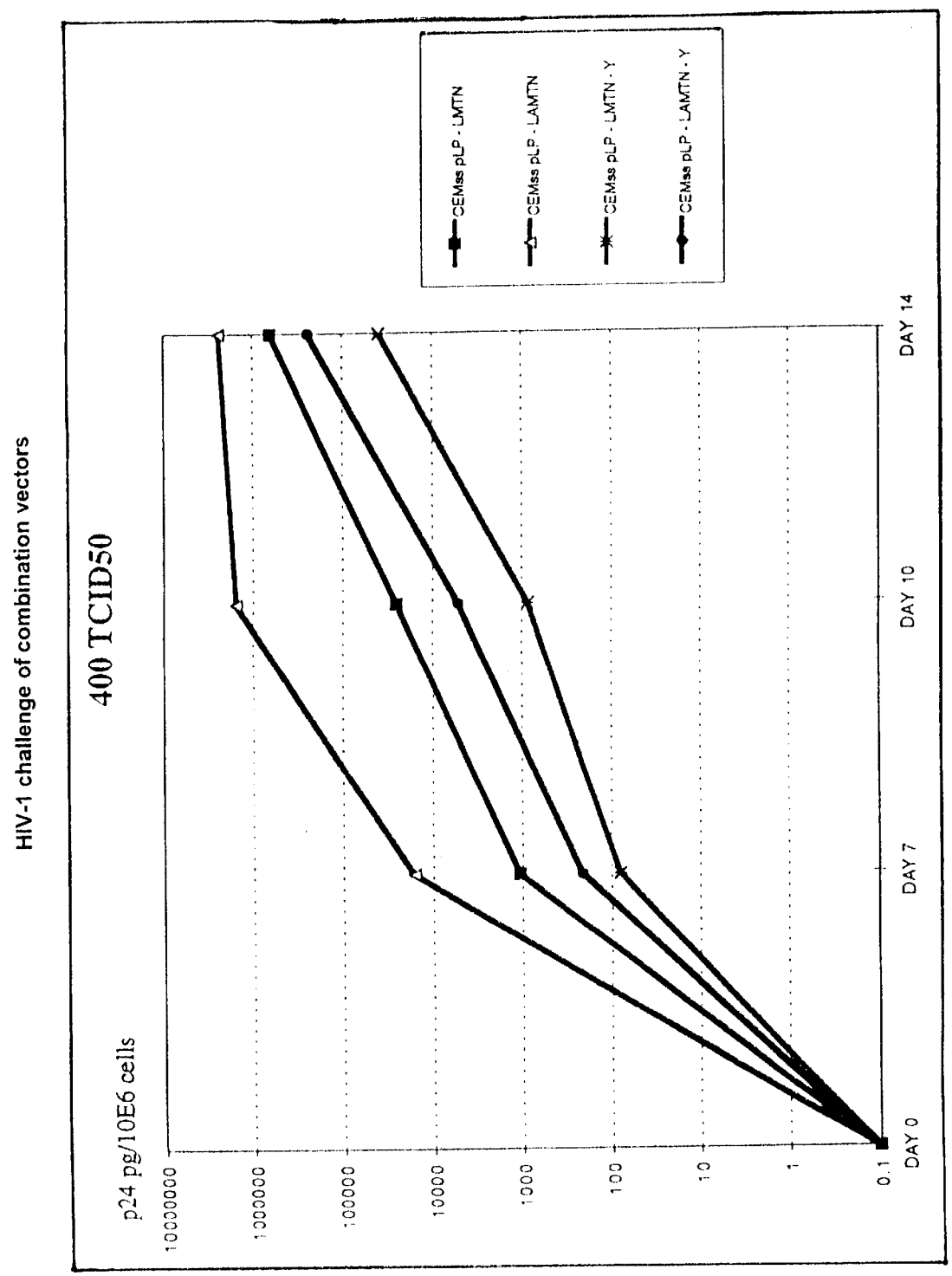
FIG. 13 depicts HIV-1 challenge of combination vectors. The two parental vectors LMTNL with the RevM10 gene and the LAMTNL with ATG less RevM10 gene as a control and the corresponding combination vectors LMTNL-Y and LAMTNL-Y with the full length, 1.5 kb psi-gag sequence in antisense orientation are challenged with 400 TCID50 HIV-1.
Figure 14:
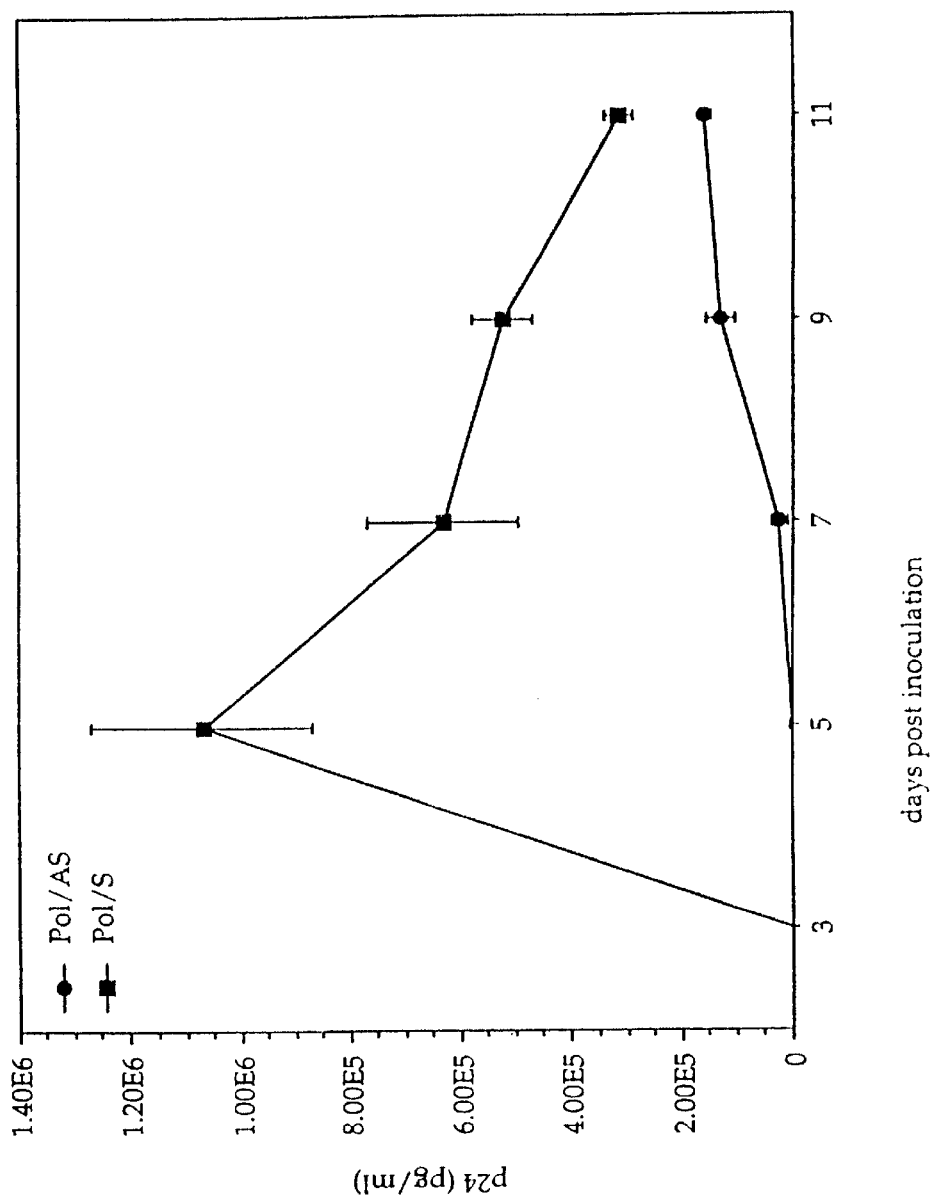
FIG. 14 depicts pol antisense mediated inhibition of HIV replication in peripheral blood lymphocytes.

Construction of Retroviral Vectors Carrying Antisense HIV-1 Sequences

Retroviral vector constructs with different antisense HIV-1 sequences are generated as follows using as parental vector pLN, described in A. Dusty Miller and Guy J. Rosman (1989) BioTechniques 7. 980–986.

a) 2LN-gag/AS vector: The 1420 bp SacI-BglII (675 bp-2095 bp) fragment is isolated from the HXB-2 strain of HIV-1 and inserted as a blunt end fragment in antisense orientation into the blunt ended HindIII site of the pLN-1 vector. Orientation of the fragment is determined by restriction digest with ClaI.

b) 3' Deletion pLN-gai/AS vectors: Serial deletion fragments from the 1420 bp SacI-BglII (675 bp-2095 bp) fragment are generated by PCR amplification. The 5' end of the fragments are fixed using the GAGCTCTCTCGACG-CAGGACT (SEQ. ID. NO. 4) primer at position 675 bp-695 bp). The primers at the 3' end were the following; primer 3.6: position 1897–1900

GTAGGATCCGTTACTTGGCTCATTGCTTCA (SEQ. ID. NO. 5); primer 3.5: position 1677–1700.

CACGGATCCGAGTTTATAGAACCGGTCTAC (SEQ. ID. NO. 6); primer 3.4: position 1479–1500

GTAGGATCCACTGCTATGTCACTTCCCCTTGG (SEQ. ID. NO. 7); primer 3.3 position 1280–1300, GTAGGATCCACATGGGTATCACTTCTGGGCTG (SEQ. ID. NO. 8); primer 3.2 position 1079–1100, GTAGGATCCTCTATCTFGTCTAAAGCTTCCTTG (SEQ. ID. NO. 9); primer 3.1 position 884–904, GTAGGATCCCCTGCTTTGCCCATACTATATG (SEQ. ID. NO. 10). The PCR fragments with BamHI and blunt end are cloned into the BamHI-HpaI site of the pLN vector. The generated fragments are approximately 1200 bp, 1000 bp, 800 bp, 600 bp, 400 bp 200 bp in length.

c) Removal of the psi sequence from the gag fragment: The 1420 bp SACI-BglII (675 bp-2095 bp) fragment is digested with Pvu II resctriction endonuclease which removes 494 bp corresponding to the psi packaging signal form the 5' end of the fragment. The resulting fragment (gag 500/AS and gag 1000/AS) is cloned as a blunt end fragment into the HindII of pLN vector.

d) pLN-Vif/AS vector: The 1100 bp EcoRI-EcoRi fragment (4646-5742) from the HXB-2 strain of HIV-1 corresponding Vif-Vpr gene of the virus is inserted into the HindII site of pLN vector in antisense orientation.

e) pLN-pol1 /AS vector: The 1480 bp ApaI-PflmI fragment (2005-3485) from the HXB-2 strain of HIV-1 corresponding to the 5' end of the Pol gene of the virus is inserted into the HindII site of pLN vector in antisense orientation.

f) pLN-pol2/AS vector: The 1250 bp PflmI-EcoRI fragment (3485-4646) from the HXB-2 strain of HIV-1 corresponding to the 3' end of the Pol gene of the virus is inserted into the HindII site of pLN vector in antisense orientation.

g) pLN-env/AS vector: The 1440 bp ApaLI-BsmI fragment (6615-8053) from the HXB-2 strain of HIV-1 corresponding to intronic region of the Env gene of the virus is inserted into the HindII site of pLN vector in antisense orientation.

h) pLN-pol1 (AS)-env(AS) vector: The pol1 fragment of e) is inserted 5' to the env construct of g), both in antisense orientation in the HindII site of the pLN vector (FIG. 12).

i) pLN3' LTR/AS vector: the 1260 bp BamHI-HindIII fragment (8474-9615) from the HXB-2 strain of HIV-1 corresponding to the 3'LTR of the virus is inserted into the XhoI site of pLN vector in antisense orientation.

j) The retroviral vector pLN-pol12/AS with the full length pol sequence is constructed by inserting the 2,642 bp ApaI-EcoRI fragment into the pLN vector in reverse orientation. For the sense control vectors pLN-pol1/S and pLN-pol12/S the 1,400 bp ApaI-PflmI and 2,642 bp ApaI-EcoRI pol fragments are cloned in the sense orientation into the pLN vector. The pLN-790pol/AS vector is constructed by inserting the 790 bp BglIIH-NsiI subfragment of the pol gene into the XhoI site of the pLN vector. Retroviral vectors (pLLyt2-pol1/AS, pLLyt2-pol1/S, pLLyt2-env/AS and pLLyt2-env/S) are constructed by replacing the Neo gene with the truncated mouse CD8 (Lyt2) cell surface marker (Forestell, S. P., et al 1997. Novel retroviral packaging cell lines: complementary tropism and improved vector production for efficient gene transfer. Gene Ther. 4:19–28) and used for the primary T cell HIV-infection experiments.

k) Combination vectors: The LMTNL and the LAMTNL vectors carrying the transdominant RevM10 gene and its ATG-less form (ΔM) (Escaich, S.; Kalfoglou, C.; Lavec, I.;et. al. Human Gene Therapy 1995. 6 625–634) are digested with ClaI and the 1200 bp ClaI-BglII fragment from HXB-2 strain of HIV-1, corresponding to the Gag gene region, is inserted as an antisense fragment.

l) Retroviral vector production: 10 ug of retroviral DNA is transfected into the ecotropic BOSC packaging line using the CaPO4 transfection protocol. The transient ecotropic viral supernatant is used to transduce the arnphotropic PA 317 packaging cell line. Since the pLN vectors carry the Neo gene, the cells are selected on G418. After selection the stable cells pools are analysed by Northern blot for the antisense RNA expression. Viral supernatants from the selected PA317 cell lines carrying the appropriate retroviral constructs are collected, analysed for transducing viral titer, and used to transduce the human CD4+T cells line CEMSS. GP47 could be used instead of BOSC as the packaging line (Rigg , R. J., et al 1996. A novel human amphotropic packaging cell line: high titer, complement resistance, and improved safety Virology. 218: 290–295). Supernatant from the GP47 packaging cell lines is used to transduce the amphotropic ProPakA cell line (Rigg, R. J., et al . 1996) by spinoculation as described previously (Forestell, S. P et al . 1997. Novel retroviral packaging cell lines: complementary tropism and improved vector production for efficient gene transfer. Gene Ther. 4:19–28). Retroviral end-point titers are determined on NIH3T3 cells after drug selection (800 mg/ml G418) and transduction efficacy of the Lyt2 vectors (Forestell, S. P et al . 1997) is measured by FACS analysis.

m) Target cell transduction: The human CD4+T cell line CEM SS cells ($2\times10^6$ cells) are transduced with the amphotropic viral supernatants carrying the antisense vector constructs in 5 ml DMEM+10FCS+8 ug/ml polybrene for 4–6 hours. 48 hours later the cells are selected on 400 ug/ml G418. After G418 selection (7–10 days) the resistant cell are expanded, the antisense RNA expression is analysed by Northern blot. The selected CEM SS cell pools are also analysed for the presence of the CD4 cell surface marker.

Example 2

HIV-1 Challenge of CEM Clones or Pools

The resistance of transduced CEM cells to HIV replication and to cytopathic effects of the virus is determined as follows:

Cells are subjected to HIV-1 infection (HXB3) in vitro. Antiviral effect is measured by cell viability, levels of p24 Ag produced in the supernatant, and levels of CD4 expression at the cell surface. Infection is measured by PCR for HIV sequences. In addition to the clones to be challenged, CEMss containing a vector control are submitted to infection by HIV-1.

Day-1: Prior to challenge the clones are tested for CD4 expression by FACS analysis.

Day 0:
1. Count the cell
2. Spin down $2\times10^6$ CEM cells 5 min at 1200 rpm
3. Pour off the supernatant from the cells
4. Dilute virus stock in culture medium to 4000 or 400 $TCID_{50/ml}$ (medium: RPMI 1640, 10% CCS, Peni 100 U/ml, Strepto 100 mg/ml)
5. Resuspend the cell pellet ($2\times10^6$ cells) in 2 ml of the virus dilution, (or 2 ml of media for the non infected control)
6. Incubate on rotator (low speed 18 rpm) for 2 hours at RT
7. Spin down the cells
8. Aspirate carefully the virus suspension
9. Wash the cells twice in 7 ml medium, by centifugation at 1200 rpm for 10 min
10. Resuspend the cells in 10 ml media (CEM at $2\times10^5$/ml final concentration)
11. Incubate at 37°c, 5% $CO_2$ for 4 days Day 4:
12. Analysis:—cell count
—1 ml of centrifuged supernatant for p24 titration, freeze at –70° C.
13. Passage the cells: dilution to $2\times10^5$/ml final in fresh medium Day 8:
14. Analysis at day 8:
—cell count
—1 ml of centrifuged supernatant for p24 titration, freeze at –70° C.
—take $10^6$ cells for CD4 staining (optional)
—lyse $2\times10_6$ cells in 400 ul for DNA PCR, store at –20° C. (optional)
—RNA extraction from $4\times10^6$ cells using RNazol, store at –70° C. (optional)
15. Passage the cells: dilution to $2\times10^5$/ml final in fresh medium
16. Cells are passaged every 4–5 days to be maintained in log phase growth until day 16 or until the controls are dead. For each passage, cells are counted and supernatant is frozen.

Example 3

Detection of Intracellular Tat and p24

Transduced CEM-SS cells expressing RevM10 and antisense HIV-1 sequences are inoculated with $1\times10^5$ $TCID_{50/10}^6$ cells/ml of HIV-1. At day 4, day 6 and day 8, cells removed from the culture, washed and resuspended in cold PBS and fixed in ice cold methanol for 30 min. The fixed cells are stained with a FITC-conjugated anti-p24 monoclonal antibody (Coulter KC57) for intracellular p24 detection, include p24, with mouse anti-Tat IgGI antibody (Repligen) for intracellular Tat detection as described earlier (Rigg, R. J., et al 1995. Detection of intracellular HIV-1 Rev protein by flow cytometry. J. Immun. Methods. 188:187–195). The samples are analyzed using a Becton-Dickinson FACScan.

Example 4

Detection of Antisense RNA in Cells

Total cellular RNA from CEM-SS cells and from activated PBLs is extracted with RNAzol (Cinna/Biotecx). 10 mg RNA is fractionated on 1.2% agarose/formaldehyde gels, transferred to Hybond N membrane (Amersham), and hybridized in Rapid-hyb buffer (Amersham). Oligonucleotides (100 ng) are radiolabeled with terminal transferase (Boehringer MA), using a-$^{32}$P-dATP to a specific activity of $3\times10^8$ cpm/mg. DNA fragments are labeled by random priming (Boehringer MA). The membranes are hybridized with the labeled probe ($5\times10^6$ cpm/ml) at 65° C. for 1 hour and washed with 1×SSC, 0.1% SDS at 65° C., and exposed on X-ray film or analyzed on a PhosphorImager (Molecular Dynamics).

Example 5

Pol Antisense-mediated Inhibition of HIV-1 Replication in PBLs

Transduction and HIV-1 infection of human PBLs: PBLs are isolated from healthy donors buffy coats by gradient centrifugation. Enriched CD4+ cells are obtained by labeling bulk PBL with biotinylated aCD8+ and aCD19+ antibodies followed by depletion with streptavidin conjugated magnetic beads (Dynabeads M-280, Dynal A. S., Norway). The enriched CD4+ PBLs are stimulated with phytohemagglutinin (PHA, 5 μg/ml) on γ-irradiated allogenic feeder cells for 72 hours in Iscove's modified DMEM medium. PBLs ($2\times10^6$) are transduced by spinoculation in the presence of Polybrene (8 μg/m). After 48 hours, cells are analysed for CD4+ and Lyt2+ expression by flow cytometry using anti-CD4-FITC and anti-CD8-PE conjugated monoclonal antibodies. Lyt2+ expressing PBLs are again enriched by magnetic bead selection. After the first enrichment, PBLs are expanded, and the CD4+/Lyt2+ cells are isolated using fluorescence-activated cell sorting (FACS, Beckton-Dickinson, Vantage). After the second enrichment, greater than 90% of the cell population is CD4 and Lyt2+. Primary CD4+T-cells ($5\times10^4$) are inoculated with 600 $TCID_{50}$/ml HIV-1 JR-CSF (5) in quadruplicate 4 days after the last restimulation of the cells. Half of the culture supernatant is exchanged daily for 9 days. Supernatants are stored at –70° C., and p24 Ag is determined by ELISA. Viable cells are counted by trypan blue exclusion 7 days after inoculation.

Example 6

Inhibition of HIV-1 Replication in CEM-SS Cells

Figure 16:
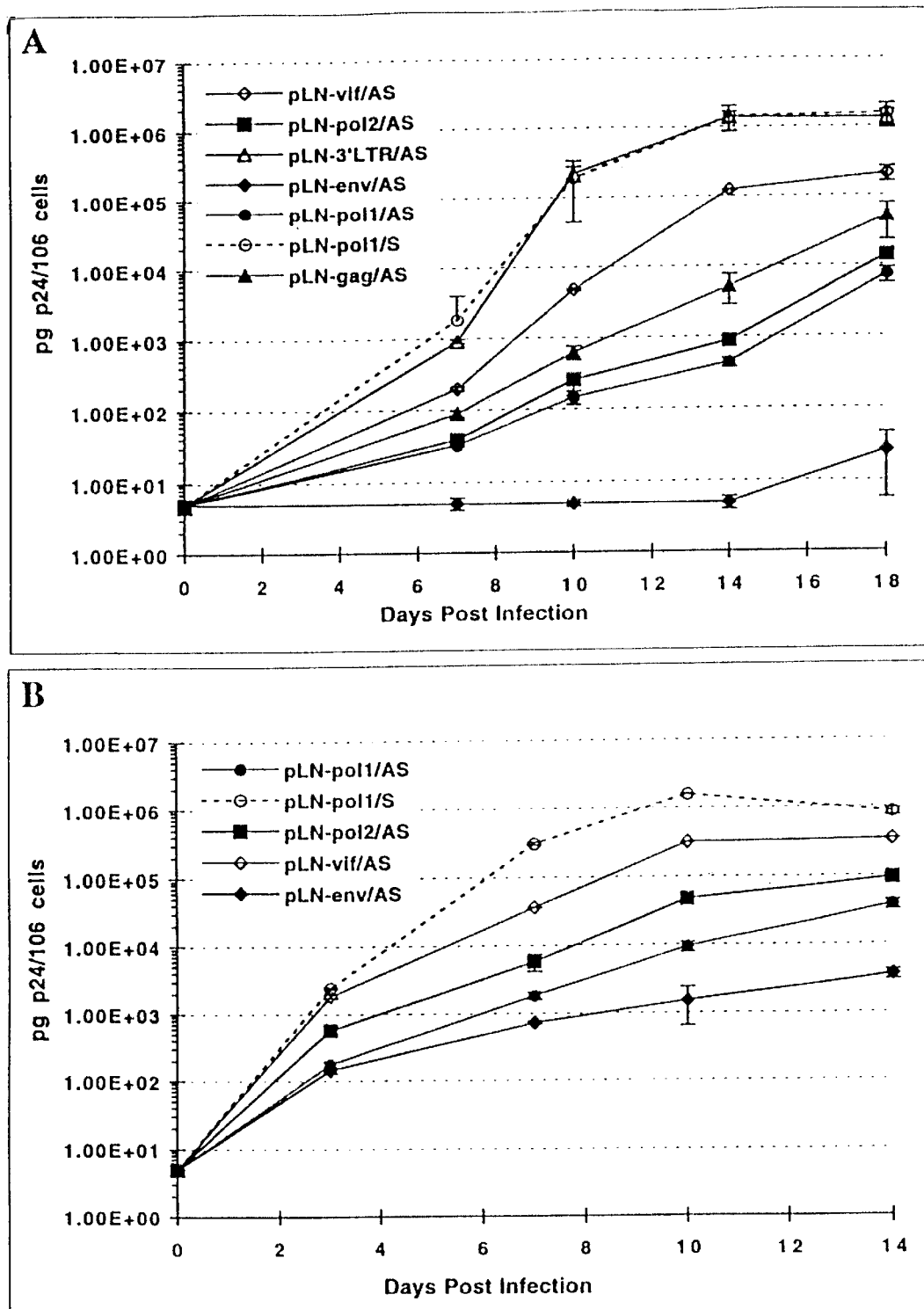
FIG. 16. Inhibition of HIV-1 replication in transduced CEM-SS cells. A: CEM-SS cell populations ($1 \times 10^6$ cells/ml) are inoculated with $4 \times 10^2$ TCID$_{50}$/ml of HIV-1 HXB3 strain. B: Increasing HIV-1 dose, $4 \times 10^4$ TCID$_{50}$/ml infection of transduced CEM-SS cell populations. The culture supernatants are tested for p24 antigen production by ELISA. experiments are done in duplicates.

To compare the efficacy of the antisense sequences, transduced CEM-SS cells expressing complementary transcripts are infected with $4\times10^2$ TCID$_{50}$/ml of the HIV-1 HXB3 virus. HIV-1 replication is monitored by measuring p24 antigen levels in the culture supernatant by ELISA. As negative control, a vector encoding the pol sequence in sense orientation (pLN-pol/S) is used. FIG. 16A shows the relative efficacy of the different antisense sequences at low HIV-1 inoculation dose. CEM-SS cells expressing the env antisense RNA showed almost complete suppression of HIV-1 replication, releasing 50 pg of p24/$10^6$ cells at day 18 post-inoculation. We have observed 3.0 log$_{10}$ reduction of p24 antigen production with the pol1 and pol2 antisense sequences and 1.0 log$_{10}$ reduction with the vif antisense sequence. The 3'LTR antisense construct is indistinguishable from the control vector, which correlates with the low expression level of antisense transcript observed by Northern blot (FIG. 15B.). In the following experiment, we increased the HIV-1 inoculation dose 100-fold to $4\times10^4$ TCID$_{50}$/ml and tested only the pol1, pol2, vif and env antisense constructs (FIG. 16B.). Overall, the onset of HIV—replication is much earlier and the replication kinetics are much faster than in the low MOI experiment. At day 10, the control CEM-SS cells(pLN-pol1/S) released high levels of p24 antigen in the culture supernatants ($2\times10^6$ pg p24/$10^6$ cells). However, at this time point HIV-1 virus replication is still substantially inhibited in all antisense CEM-SS cultures relative to control, Although, HIV replication levels are higher than in the previous experiment, intracellular env expression is again the most potent inhibitor (3.0 log$_{10}$ reduction) followed by pol1 and pol2 (2.0 log$_{10}$ reduction) and the antisense vif sequence is the least potent antiviral inhibitor (1.0 log$_{10}$ reduction). Similar results are observed when antisense RNA expressing CEM-SS cells are infected with the less cytopathic SF2 HIV-1 strain (data not shown).

Example 7

Effect of Antisense RNA Length on HIV Inhibition.

Figure 17:
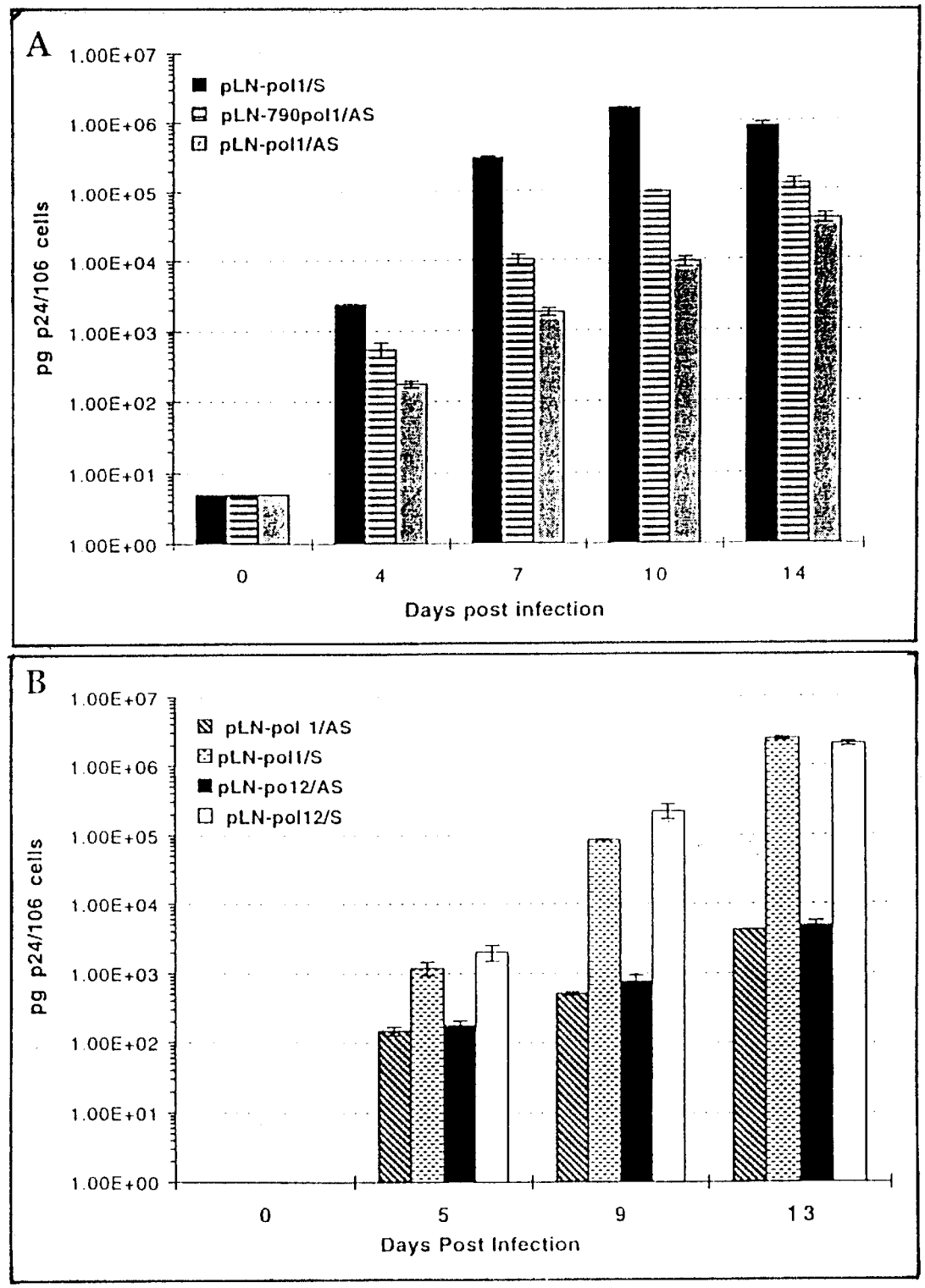
FIG. 17. Evaluation of anti-HIV-1 efficacy of vectors encoding different length complementary pol sequences. A. Anti-HIV-1 efficacy of pol1_deletion constructs. CEM-SS cells expressing the 1,400 nt pol1 and 790 nt pol antisense and the sense pol1 constructs are infected with $4 \times 10^3$ TCID$_{50}$/ml of HIV-1 HXB3 strain. B. CEM-SS cells expressing the 1,400 nt pol1 and the 2,600 nt pol12 antisense sequences are infected with $4 \times 10^3$ TCID$_{50}$/ml HIV-1 HXB3 strain. The corresponding sense constructs are used as a control.

To confirm that our observation is not specific to the Y-gag antisense RNA, a vector encoding a shorter pol antisense fragments as described in Materials and Methods is constructed. The antiviral potency of the 790 nt long antisense pol fragment and the 1,400 nt pol1 fragment is compared at $4\times10^3$ TCIDU$_{50}$/ml of HIV-1 HXB3. An approximately 50% decrease in anti-HIV-1 efficacy with the shorter pol1 sequence relative to the 1,400 nt pol1 fragment is observed as shown in FIG. 17.A. This experiment provide further evidence that the length of the retrovirally expressed antisense RNA is an important factor for antiviral efficacy.

A vector encoding an antisense transcript of the complete pol gene reading frame is also generated to address the question whether increasing the antisense RNA length beyond 1,400 nt results in increased antiviral efficacy. FIG. 17.B demonstrates that the 1,400 nt pol1 antisense sequence is as efficient in blocking HIV-1 replication as the 2,600 nt pol12 antisense RNA. Since both pol1 and pol2 antisense RNA yield comparable levels of inhibition, this experiment suggests that other factors in addition to expression level and transcript length may influence the efficacy of antisense RNA.

Example 8

Comparison of Anti-HIV-1 Efficacy of RevM10 and Antisense RNAs

Figure 19:
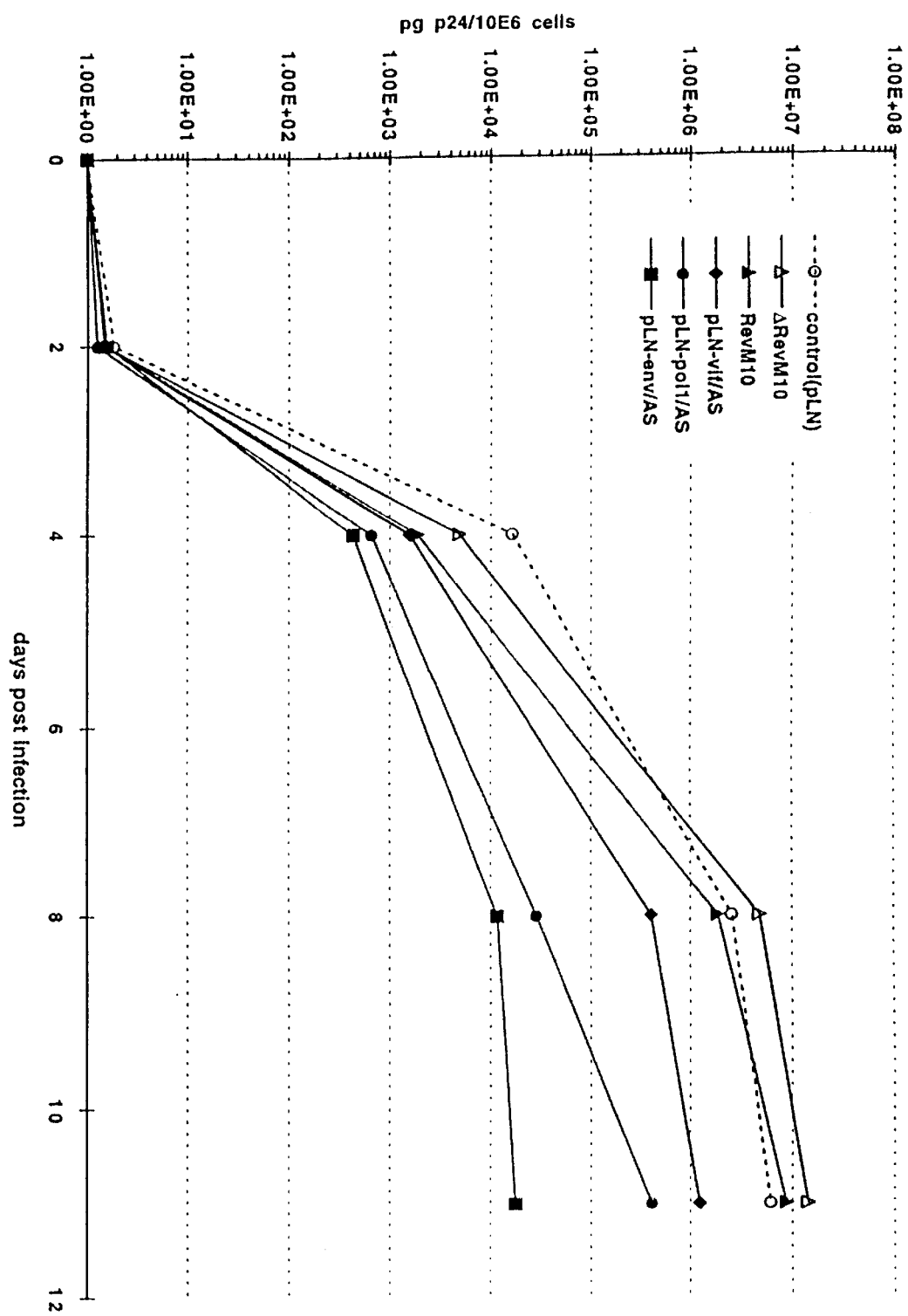
FIG. 19. Comparison of trans-dominant RevM10 and intracellularly expressed vif, pol1 and env antisense RNAs in high inoculation dose HIV-1 infection experiments. CEM-SS cells ($1 \times 10^6$/ml) are inoculated with $1 \times 10^5$ TCID$_{50}$/ml of HIV-1 HXB3 and viral replication is monitored by measuring p24 antigen production in the culture supernatant.
Figure 20:
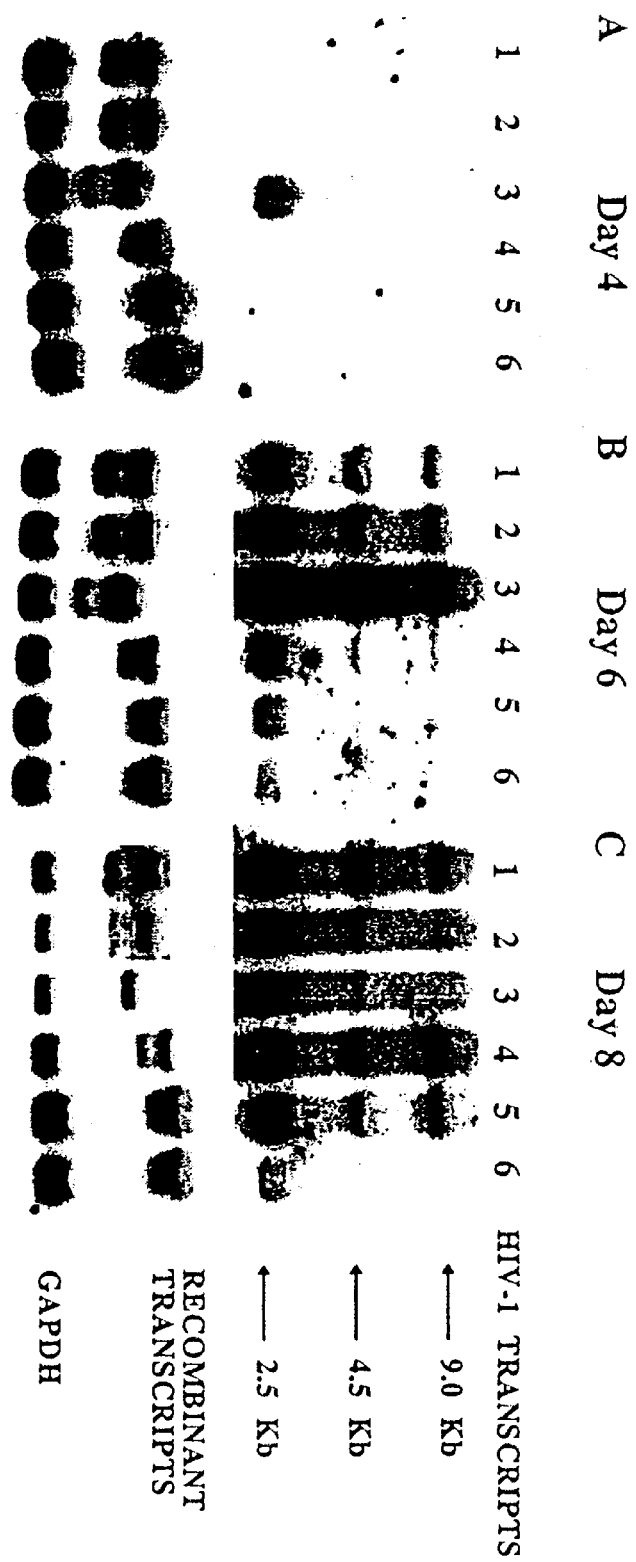
FIG. 20. Detection of HIV-1, antisense and RevM10 transcripts in CEM-SS cells inoculated with $1 \times 10^5$ TCID$_{50}$/ml HIV-1, HXB3 strain. Total cellular RNA is isolated from CEM-SS cells at day 4, day 6 and day 8 post infection. The HIV specific transcripts are analyzed on Northern blot using a radiolabeled TAR specific oligonucleotide probe. Expression of the antisense or RevM10 transcripts is determined using a Neo or a Rev specific probe respectively. A GAPDH specific probe is used to monitor the amount of RNA loaded. Lane 1: RevM10, Lane 2: DRevM10, Lane 3: pLN(vector control), Lane 4: pLN-vif/AS, Lane 5:pLN-pol1/AS, Lane 6:pLN-env/AS. Panel A: Day 4., Panel B: day 6, Panel C: Day 8.

The antiviral potency of antisense vif, pol1, and env sequences at a high HIV-1 inoculation dose with RevM10, the trans-dominant form of the HIV-1 Rev protein is compared. RevM10 acts post-transcriptionally, preventing the transport of full length HIV-1 transcripts from the nucleus to the cytoplasm. In order to test at which step the antisense RNA interferes with the HIV-1 life cycle, the effect of RevM10 and antisense RNA on HIV-1 RNA steady-state levels as well as on structural (p24 gag) and regulatory (Tat) protein expression is analyzed. Polyclonal CEM-SS cell populations expressing RevM10, DRevM10 (Plavec, I., et al 1997. High transdominant RevM10 protein levels are required to inhibit HIV-1 replication in cell lines and primary T cells: implication for gene therapy of AIDS. Gene Ther. 4:128–139) and antisense vif, pol and env sequences are inoculated with $1\times10^5$ TCID$_{50}$/$10^6$ cells HIV-1 HXB3 (MOI: 0.1). The analyses of secreted p24 antigen release into the cell supernatant indicate the rapid progression of viral replication in the control cultures (pLN and DRevM10), as well as in the RevM10 and vif/AS cell populations (FIG. 19.). In contrast, 2.0 orders of magnitude lower p24 production is observed with the pol/AS and env/AS RNA expressing cell lines. Total RNA samples isolated from HIV-1 infected cells at day 4,. day 6 and day 8 post infection are analyzed. Northern blot analyses of day 4 samples shows low levels of HIV-1 transcripts in all cultures (FIG. 20.A.). At this time point, the steady-state expression levels of all recombinant transcripts are comparable. At day 6 post infection (FIG. 20.B.), the control vector (lane 3) and DRevM10 (lane 2) transduced cells express high steady-state levels of HIV-1 transcripts. The RevM10 (lane 1) and vif/AS (lane 4) vector transduced cells express 3- to 5-fold less than the respective control cell populations, and the pol/AS (lane 5) and env/AS (lane 6) vector transduced cells still express very low HIV-1 RNA levels (FIG. 20.B.) At this time point there are still comparable amounts of recombinant transcript present in all cultures (lower panel). Analyses of the day 8 RNA samples (FIG. 20.C.) demonstrated degradation and decreased amounts of all 3 RNA transcripts analyzed (HIV-1, vector transcripts and GAPDH) in the control cell populations, probably due to the massive HIV-1 induced cell death in these cultures. High levels of HIV-1 RNA are detected in the RevM10 and vif/AS expressing cells, increased about 5-fold in the pol/AS expressing cells, but is still very low in the env/AS RNA expressing cells. At the same time point, we also analysed the intracellular p24 Gag and Tat protein levels in the infected cell population. FACS analysis of day 8 samples demonstrate that 27% of the pol/AS and only 5% of the env/AS RNA expressing cells express detectable amount of p24 Gag protein (FIG. 21.A.), which correlates with the observed low HIV transcript levels. At this time point, almost 100% of the CEM-SS cells expressing the RevM10 gene or vif/AS RNA are positive for intracellular p24 Gag protein, although the vif/AS population produced lower p24 antigen levels (mean fluorescence intensity 135).

Figure 21:
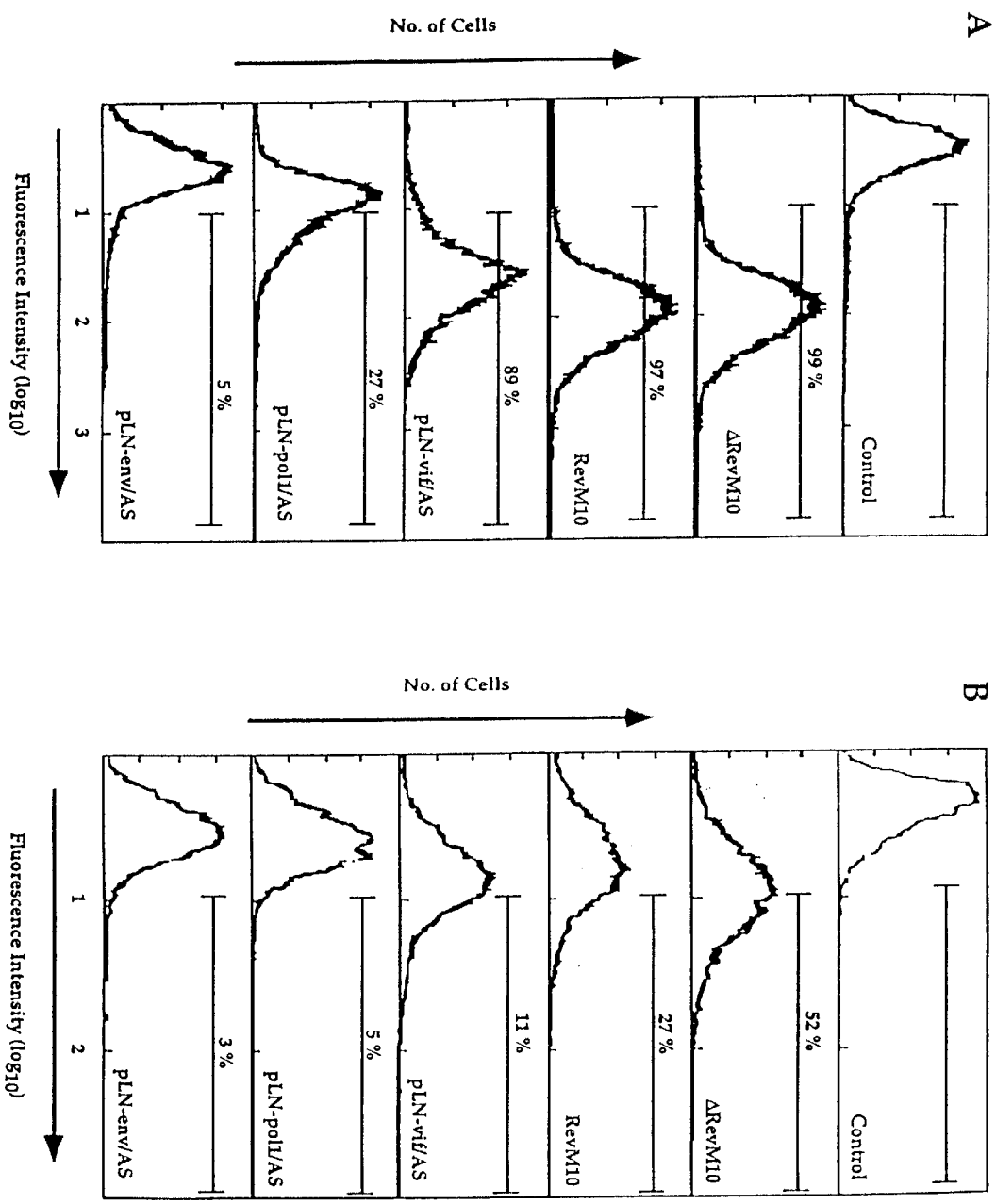
FIG. 21. Analyses of intracellular p24 and Tat expression in HIV-1 infected CEM-SS cells. A. Intracellular $p^{24}$ expression is measured at day 8 post infection. The mean fluorescence intensity reflects the relative intracellular p24 expression level. B. Detection of Tat protein in transduced and HIV-1 infected CEM-SS cells. Aliquots of infected CEM-SS cells at day 8 post infection are fixed in methanol, stained with Tat specific antibody and analyzed by FACScan.

Measuring the intracellular Tat protein levels gave similar results, although the sensitivity of this assay is lower than for the p24 Gag protein detection. FIG.21.B demonstrates that only 3–5% of antisense pol and env RNA expressing cells produce detectable Tat protein, which can explain the observed low overall HIV transcript levels.

The HIV-inhibitory effects of the vectors are depicted in FIGS. 7 through 21. Vectors containing longer antisense fragments are more effective inhibitors, as are vectors containing antisense to the tat, pot, and/or the env regions. Combination vectors containing RevM10 plus an antisense construct are more effective than vectors containing revM10 or antisense alone.

What is claimed is:

1. A nucleic acid sequence which, when stably integrated into a human cell, is capable of generating mRNA which anneals with a mRNA transcript from an HIV-1 provirus encoding env and pol or env, pol and gag, wherein the nucleic acid sequence is 1.1 to 1.5 kb in length and is antisense to the 1.4 kb fragment from the Apa1 cleavage site at ca. base 2004 of an HIV-1 provirus to the Pflm1 cleavage site ca. base 3400 of an HIV-1 provirus.

2. The nucleic acid sequence according to claim 1 which is antisense to the sequence depicted in FIG. 1 (SEQ ID NO:1).

3. A retroviral vector comprising the nucleic acid sequence according to claim 1.

4. The retroviral vector according to claim 3 further comprising at least one gene encoding for an HIV inhibitory protein.

5. The retroviral vector according to claim 4 wherein the HIV inhibitory protein is RevM10.

6. A cellular composition comprising at least one human hematopoietic cell stably transduced with the nucleic acid sequence according to claim 1 and optionally additionally stably transduced with a gene encoding for an HIV inhibitory protein.

7. The cellular composition according to claim 6 wherein the human hematopoietic cell is a hematopoietic stem cell, and the HIV inhibitory protein is RevM10.

8. A method of inhibiting HIV-1 replication in a CD4+ or hematopoletic stem cell in an HIV-1 infected patient, the method comprising
   (a) isolating the CD4+ or hematopoietic stem cell from the patient;
   (b) transducing the cell with a retroviral vector comprising the nucleic acid sequence according to claim 1; and
   (c) reintroducing the transduced cell into the patient, wherein HIV-1 replication in the cell is inhibited.

9. A retroviral vector comprising the nucleic acid sequence according to claim 2.

10. The retroviral vector according to claim 9 further comprising at least one gene encoding for an HIV inhibitory protein.

11. The retroviral vector according to claim 10 wherein the HIV inhibitory protein is RevM10.

12. A cellular composition comprising at least one human hematopoietic cell stably Adz transduced with the nucleic acid sequence according to claim 2 and optionally additionally stably transduced with a gene encoding for an HIV inhibitory protein.

13. The cellular composition according to claim 12 wherein the human hematopoietic cell is a hematopoietic stem cell, and the HIV inhibitory protein is RevM10.

14. A packaging cell line comprising the retroviral vector according to claim 3.

15. A packaging cell line comprising the retroviral vector according to claim 4.

16. A packaging cell line comprising the retroviral vector according to claim 5.

17. A packaging cell line comprising the retroviral vector according to claim 9.

18. A packaging cell line comprising the retroviral vector according to claim 10.

19. A packaging cell line comprising the retroviral vector according to claim 11.

20. A viral supernatant produced by the packaging cell line of claim 14.

21. A viral supernatant produced by the packaging cell line of claim 15.

22. A viral supernatant produced by the packaging cell line of claim 16.

23. A viral supernatant produced by the packaging cell line of claim 17.

24. A viral supernatant produced by the packaging cell line of claim 18.

25. A viral supernatant produced by the packaging cell line of claim 19.

26. The method of claim 8, wherein the retroviral vector further comprises at least one gene encoding for an HIV inhibitory protein.

27. The method of claim 26, wherein the HIV inhibitory protein is RevM10.

28. A method of inhibiting HIV-1 replication in a CD4+ or hematopoietic stem cell in an HIV-1 infected patient, the method comprising
   (a) isolating the CD4+ or hematopoletic stem cell from the patient;
   (b) transducing the cell with a retroviral vector comprising the nucleic acid sequence according to claim 2; and
   (c) reintroducing the transduced cell into the patient, wherein HIV-1 replication in the cell is inhibited.

29. The method of claim 28, wherein the retroviral vector further comprises at least one gene encoding for an HIV inhibitory protein.

30. The method of claim 29, wherein the HIV inhibitory protein is RevM10.

* * * * *

SEQUENCE LISTING

<160> NUMBER OF SEQ ID NOS: 10

<210> SEQ ID NO 1
<211> LENGTH: 1396
<212> TYPE: DNA
<213> ORGANISM: HIV-1

<400> SEQUENCE: 1

```
gggcccctag gaaaaagggc tgttggaaat gtggaaagga aggacaccaa atgaaagatt      60
gtactgagag acaggctaat ttttagggga agatctggcc ttcctacaag ggaaggccag     120
ggaattttct tcagagcaga ccagagccaa cagccccacc agaagagagc ttcaggtctg     180
gggtagagac aacaactccc cctcagaagc aggagccgat agacaaggaa ctgtatcctt     240
taacttccct caggtcactc tttggcaacg acccctcgtc acaataaaga taggggggca     300
actaaaggaa gctctattag atacaggagc agatgataca gtattagaag aaatgagttt     360
gccaggaaga tggaaaccaa aaatgatagg gggaattgga ggttttatca agtaagaca      420
gtatgatcag atactcatag aaatctgtgg acataaagct ataggtacag tattagtagg     480
acctacacct gtcaacataa ttggaagaaa tctgttgact cagattggtt gcactttaaa     540
ttttcccatt agccctattg agactgtacc agtaaaatta aagccaggaa tggatggccc     600
aaaagttaaa caatggccat tgacagaaga aaaaataaaa gcattagtag aaatttgtac     660
agagatggaa aaggaaggga aaatttcaaa aattgggcct gaaaatccat acaatactcc     720
agtatttgcc ataaagaaaa agacagtac taaatggaga aaattagtag atttcagaga     780
acttaataag agaactcaag acttctggga agttcaatta ggaataccac atcccgcagg     840
gttaaaaaag aaaaaatcag taacagtact ggatgtgggt gatgcatatt tttcagttcc     900
cttagatgaa gacttcagga agtatactgc atttaccata cctagtataa acaatgagac     960
accagggatt agatatcagt acaatgtgct tccacaggga tggaaaggat caccagcaat    1020
attccaaagt agcatgacaa aaatcttaga gccttttaga aaacaaaatc cagacatagt    1080
tatctatcaa tacatggatg atttgtatgt aggatctgac ttagaaatag ggcagcatag    1140
aacaaaaata gaggagctga gacaacatct gttgaggtgg ggacttacca caccagacaa    1200
aaaacatcag aaagaacctc cattcctttg gatgggttat gaactccatc ctgataaatg    1260
gacagtacag cctatagtgc tgccagaaaa agacagctgg actgtcaatg acatacagaa    1320
gttagtgggg aaattgaatt gggcaagtca gatttaccca gggattaaag taaggcaatt    1380
atgtaaactc cttaga                                                    1396
```

<210> SEQ ID NO 2
<211> LENGTH: 1250
<212> TYPE: DNA
<213> ORGANISM: HIV-1

<400> SEQUENCE: 2

```
ggaaccaaag cactaacaga agtaatacca ctaacagaag aagcagagct agaactggca     60
gaaaacagag agattctaaa agaaccagta catggagtgt attatgaccc atcaaaagac    120
ttaatagcag aaatacagaa gcaggggcaa ggccaatgga catatcaaat ttatcaagag    180
ccatttaaaa atctgaaaac aggaaaatat gcaagaatga gggtgcccca cactaatgat    240
gtaaaacaat taacagaggc agtgcaaaaa ataaccacag aaagcatagt aatatgggga    300
aagactccta aatttaaact gcccatacaa aaggaaacat gggaaacatg gtggacagag    360
```

-continued

```
tattggcaag ccacctggat tcctgagtgg gagtttgtta ataccccctcc cttagtgaaa        420
ttatggtacc agttagagaa agaacccata gtaggagcag aaaccttcta tgtagatggg        480
gcagctaaca gggagactaa attaggaaaa gcaggatatg ttactaatag aggaagacaa        540
aaagttgtca ccctaactga cacaacaaat cagaagactg agttacaagc aatttatcta        600
gctttgcagg attcgggatt agaagtaaac atagtaacag actcacaata tgcattagga        660
atcattcaag cacaaccaga tcaaagtgaa tcagagttag tcaatcaaat aatagagcag        720
ttaataaaaa aggaaaaggt ctatctggca tgggtaccag cacacaaagg aattggagga        780
aatgaacaag tagataaatt agtcagtgct ggaatcagga aagtactatt tttagatgga        840
atagataagg cccaagatga acatgagaaa tatcacagta attggagagc aatggctagt        900
gattttaacc tgccacctgt agtagcaaaa gaaatagtag ccagctgtga taaatgtcag        960
ctaaaaggag aagccatgca tggacaagta gactgtagtc caggaatatg gcaactagat       1020
tgtacacatt tagaaggaaa agttatcctg gtagcagttc atgtagccag tggatatata       1080
gaagcagaag ttattccagc agaaacaggg caggaaacag catattttct tttaaaatta       1140
gcaggaagat ggccagtaaa aacaatacat actgacaatg gcagcaattt caccggtgct       1200
acggttaggg ccgcctgttg gtgggcggga atcaagcagg aatttggaat                  1250
```

<210> SEQ ID NO 3
<211> LENGTH: 1391
<212> TYPE: DNA
<213> ORGANISM: HIV-1

<400> SEQUENCE: 3

```
cactgatttg aagaatgata ctaataccaa tagtagtagc gggagaatga atggagaa         60
aggagagata aaaaactgct ctttcaatat cagcacaagc ataagaggta aggtgcagaa       120
agaatatgca ttttttata acttgatat aataccaata gataatgata ctaccagcta        180
tagcttgaca agttgtaaca cctcagtcat tacacaggcc tgtccaaagg tatccttga        240
gccaattccc atacattatt gtgccccggc tggttttgcg attctaaaat gtaataataa       300
gacgttcaat ggaacaggac catgtacaaa tgtcagcaca gtacaatgta cacatggaat      360
taggccagta gtatcaactc aactgctgtt aaatggcagt ctagcagaag aagaggtagt      420
aattagatct gtcaatttca cggacaatgc taaaaccata atagtacagc tgaacacatc      480
tgtagaaatt aattgtacaa gacccaacaa caatacaaga aaaagaatcc gtatccagag      540
aggaccaggg agagcatttg ttacaatagg aaaaatagga aatatgagac aagcacattg      600
taacattagt agagcaaaat ggaataacac tttaaaacag atagatagca aattaagaga      660
acaattcgga aataataaaa caataatctt taagcaatcc tcaggagggg acccagaaat      720
tgtaacgcac agttttaatt gtggagggga attttctac tgtaattcaa cacaactgtt       780
taatagtact tggtttaata gtacttggag tactgaaggg tcaataaca ctgaaggaag       840
tgacacaatc accctcccat gcagaataaa acaaattata aacatgtggc agaaagtagg      900
aaaagcaatg tatgcccctc ccatcagtgg acaaattaga tgttcatcaa atattacagg      960
gctgctatta acaagagatg gtggtaatag caacaatgag tccgagatct tcagacttgg     1020
aggaggagat atgagggaca attggagaag tgaattatat aaatataaag tagtaaaaat      1080
tgaaccatta ggagtagcac ccaccaaggc aaagagaaga gtggtgcaga gagaaaaaag     1140
agcagtggga ataggagctt tgttccttgg gttcttggga gcagcaggaa gcactatggg     1200
```

-continued

```
cgcagcctca atgacgctga cggtacaggc cagacaatta ttgtctggta tagtgcagca    1260
gcagaacaat ttgctgaggg ctattgaggc gcaacagcat ctgttgcaac tcacagtctg    1320
gggcatcaag cagctccaag caagaatcct agctgtggaa agatacctaa aggatcaaca    1380
gctcctagca s                                                         1391
```

<210> SEQ ID NO 4
<211> LENGTH: 21
<212> TYPE: DNA
<213> ORGANISM: HIV-1

<400> SEQUENCE: 4

```
gagctctctc gacgcaggac t                                              21
```

<210> SEQ ID NO 5
<211> LENGTH: 30
<212> TYPE: DNA
<213> ORGANISM: HIV-1

<400> SEQUENCE: 5

```
gtaggatccg ttacttggct cattgcttca                                     30
```

<210> SEQ ID NO 6
<211> LENGTH: 31
<212> TYPE: DNA
<213> ORGANISM: HIV-1

<400> SEQUENCE: 6

```
cacggatccg agttttatag aaccggtcta c                                   31
```

<210> SEQ ID NO 7
<211> LENGTH: 32
<212> TYPE: DNA
<213> ORGANISM: HIV-1

<400> SEQUENCE: 7

```
gtaggatcca ctgctatgtc acttcccctt gg                                  32
```

<210> SEQ ID NO 8
<211> LENGTH: 32
<212> TYPE: DNA
<213> ORGANISM: HIV-1

<400> SEQUENCE: 8

```
gtaggatcca catgggtatc acttctgggc tg                                  32
```

<210> SEQ ID NO 9
<211> LENGTH: 33
<212> TYPE: DNA
<213> ORGANISM: HIV-1

<400> SEQUENCE: 9

```
gtaggatcct ctatcttgtc taaagcttcc ttg                                 33
```

<210> SEQ ID NO 10
<211> LENGTH: 30
<212> TYPE: DNA
<213> ORGANISM: HIV-1

<400> SEQUENCE: 10

```
gtaggatccc ctgcttgccc atactatatg                                     30
```